United States Patent
Morita et al.

(10) Patent No.: US 12,128,167 B2
(45) Date of Patent: Oct. 29, 2024

(54) ATTACHING MEMBER

(71) Applicant: Nikkiso Company Limited, Tokyo (JP)

(72) Inventors: Masayuki Morita, Shizuoka (JP); Shunsuke Kawamura, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 693 days.

(21) Appl. No.: 17/350,414

(22) Filed: Jun. 17, 2021

(65) Prior Publication Data

US 2021/0308357 A1 Oct. 7, 2021

Related U.S. Application Data

(63) Continuation of application No. PCT/JP2019/051339, filed on Dec. 26, 2019.

(30) Foreign Application Priority Data

Dec. 27, 2018 (JP) .................................. 2018-246176

(51) Int. Cl.
*A61M 1/36* (2006.01)
*A61M 1/14* (2006.01)
(Continued)

(52) U.S. Cl.
CPC .............. *A61M 1/367* (2013.01); *A61M 1/14* (2013.01); *A61M 1/3424* (2014.02);
(Continued)

(58) Field of Classification Search
CPC ...... A61M 1/367; A61M 1/14; A61M 1/3424; A61M 60/113; A61M 60/279;
(Continued)

(56) References Cited

U.S. PATENT DOCUMENTS 5,427,509 A * 6/1995 Chapman ........ A61M 1/362261
604/153
5,928,177 A * 7/1999 Brugger .............. A61M 60/279
604/6.11
(Continued)

FOREIGN PATENT DOCUMENTS

EP 0694125 B1 2/1999
EP 1671665 A1 6/2006
(Continued)

OTHER PUBLICATIONS

Potentially related to U.S. Appl. No. 17/347,852, filed Jun. 15, 2021, and previsouly published as WO2020/137016 A1.
(Continued)

*Primary Examiner* — Catharine L Anderson
*Assistant Examiner* — Erin A Kim
(74) *Attorney, Agent, or Firm* — Young Basile Hanlon & MacFarlane, P.C.

(57) ABSTRACT

The present teachings provide an attaching member to be attached to a blood purification apparatus including peristaltic pumps, the attaching member holding pump tubes to be squeezed in a predetermined direction by the respective peristaltic pumps for liquid delivery. The attaching member includes a body attachable to a predetermined position of the blood purification apparatus, and holding portions attached to the body and that hold the pump tubes. The holding portions are attached to edge portions on two opposite sides of the body, and flexible tubes that each allow liquid to flow through are to be placed in a central portion of the body, the central portion being positioned between the holding portion on one of the edge portions and the holding portion on the other of the edge portions.

7 Claims, 22 Drawing Sheets

(51) Int. Cl.
  *A61M 1/34* (2006.01)
  *A61M 60/113* (2021.01)
  *A61M 60/279* (2021.01)
  *A61M 60/37* (2021.01)

(52) U.S. Cl.
  CPC ........ *A61M 60/113* (2021.01); *A61M 60/279* (2021.01); *A61M 60/37* (2021.01); *A61M 2209/082* (2013.01)

(58) Field of Classification Search
  CPC ............ A61M 60/37; A61M 2209/082; A61M 1/1524; A61M 1/155; A61M 1/15; A61M 1/152; A61M 1/156; A61M 1/1561; A61M 1/3622; A61M 60/847; A61M 205/12; A61M 205/121; F04B 43/12; F04B 45/08
  See application file for complete search history.

(56) References Cited

U.S. PATENT DOCUMENTS

2006/0155236 A1    7/2006  Gara et al.
2017/0072122 A1*   3/2017  Mochizuki ............ A61M 39/10

FOREIGN PATENT DOCUMENTS

| EP | 2682608 A1 | 1/2014 |
|----|------------|--------|
| JP | S60-148069 U | 10/1985 |
| JP | 2005-074234 A | 3/2005 |
| JP | 2006-212050 A | 8/2006 |
| JP | 2008-000425 A | 1/2008 |
| JP | 2010-190062 A | 9/2010 |
| JP | 2015-073847 A | 4/2015 |
| JP | 2015-202248 A | 11/2015 |
| JP | 2017-140521 A | 8/2017 |
| JP | 2017-164285 A | 9/2017 |
| WO | 1995/017603 A1 | 6/1995 |
| WO | 1996/040322 A2 | 12/1996 |
| WO | 2013/090579 A1 | 6/2013 |
| WO | 2013/098028 A1 | 7/2013 |
| WO | 2018/225027 A1 | 12/2018 |

OTHER PUBLICATIONS

Potentially related to U.S. Appl. No. 17/348,037, filed Jun. 15, 2021, and previously published as WO2020/138380 A1.
Potentially related to U.S. Appl. No. 17/348,051, filed Jun. 15, 2021, and previosuly published as WO2020/138381 A1.
Potentially related patent application that will be filed with the USPTO, and is published as WO2020/138382 A1.
Potentially related patent application that will be filed with the USPTO, and is published as WO2020/138384 A1.
European Search Report for Application No. 19905343.0, dated Sep. 5, 2022, 8 pgs.

* cited by examiner

[Fig. 1]
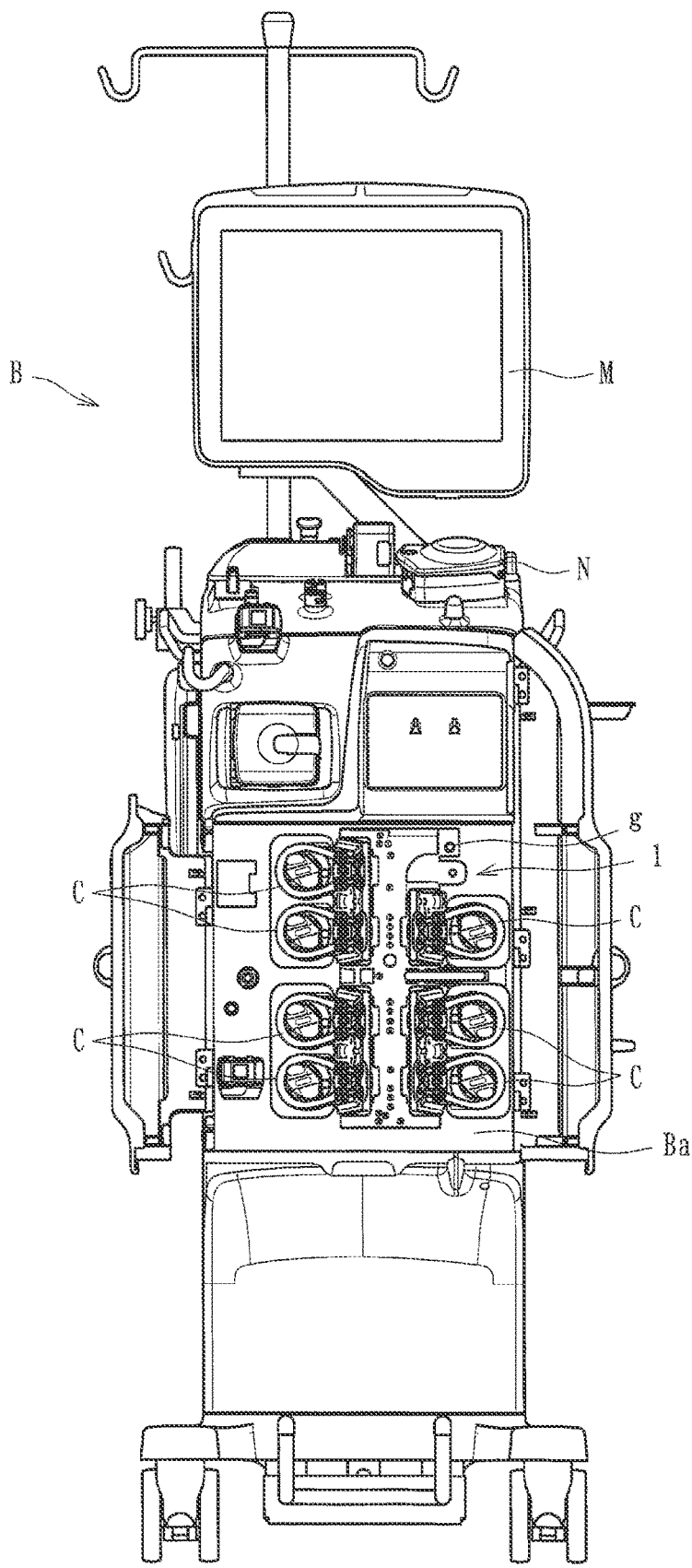

[Fig. 2]
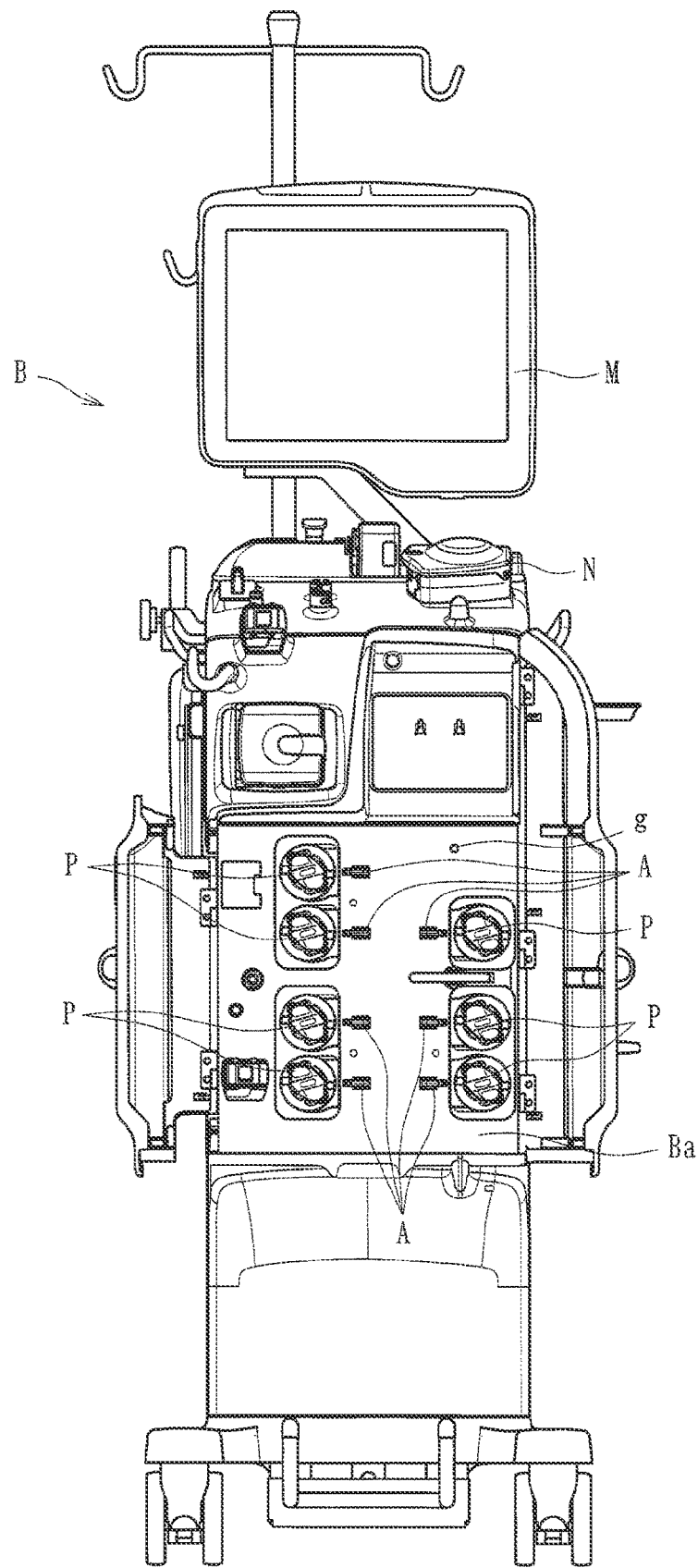

[Fig. 3]
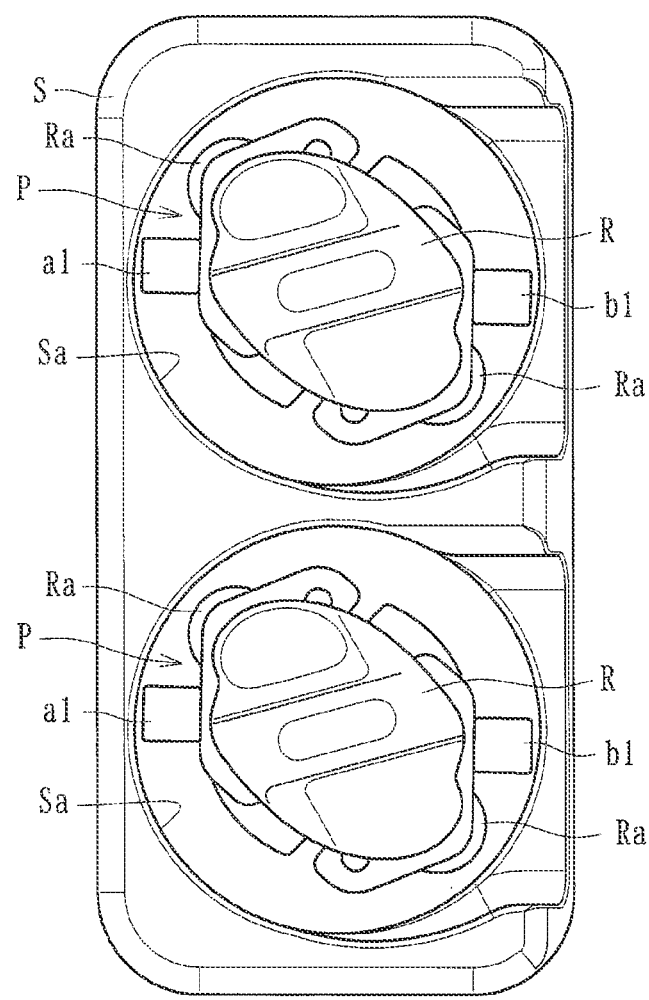

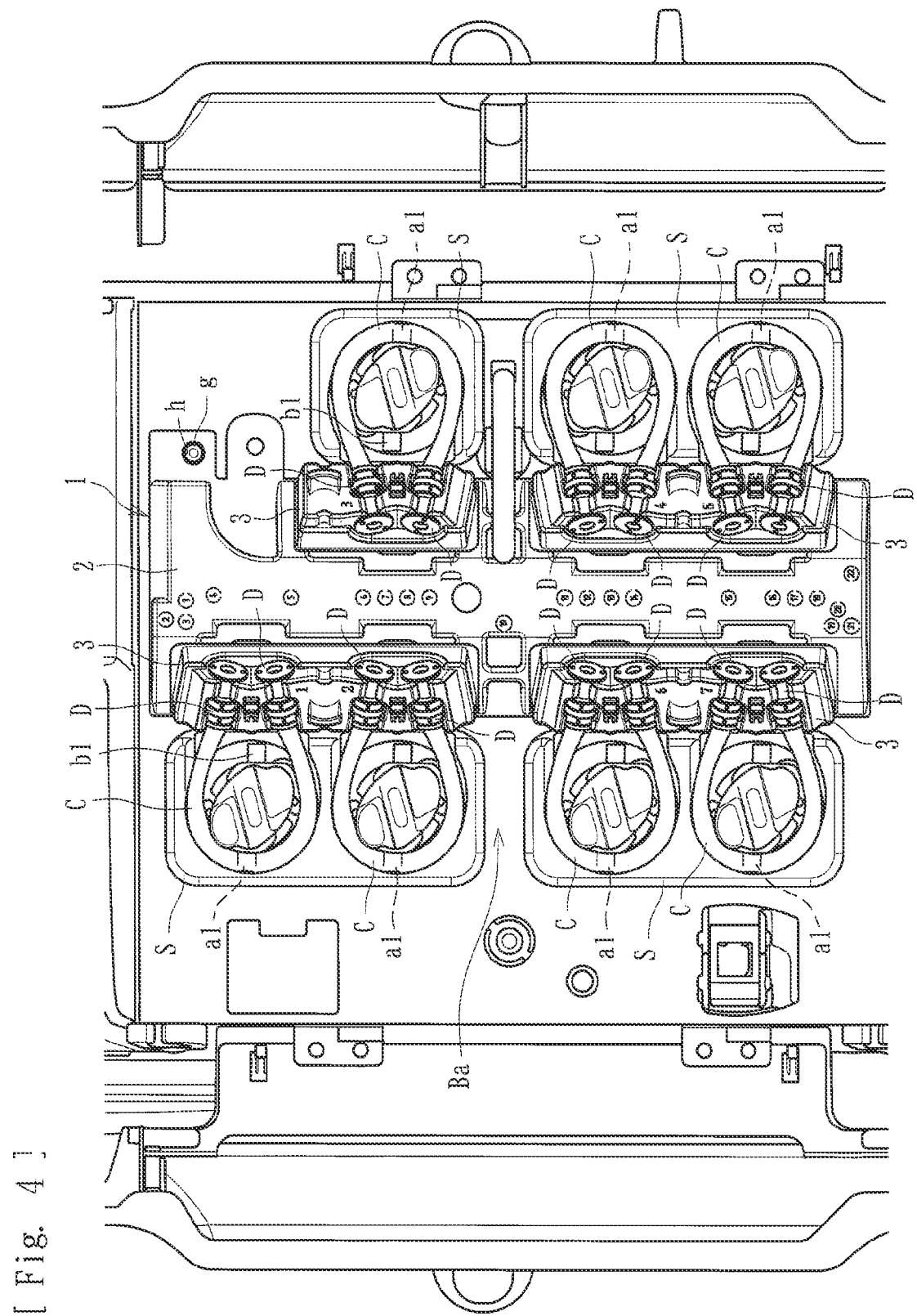
[Fig. 4]

[Fig. 5]
(a)
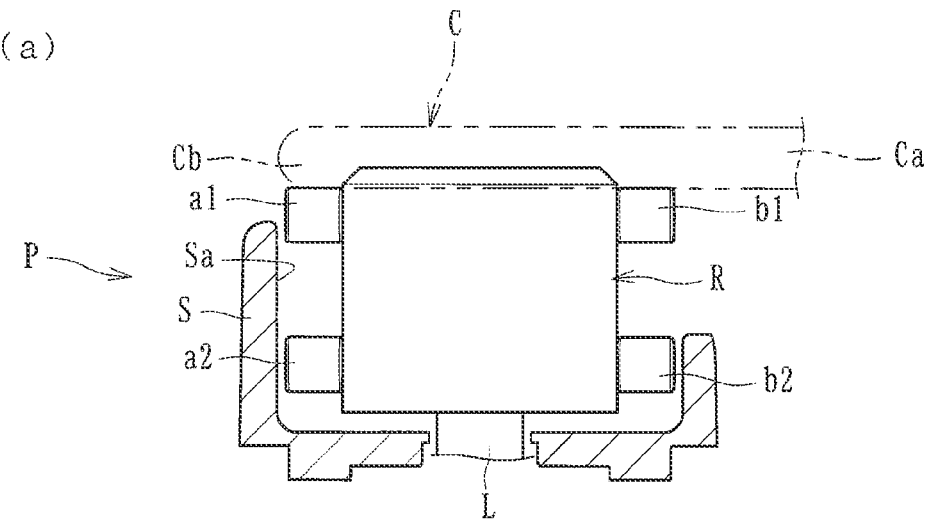
(b)
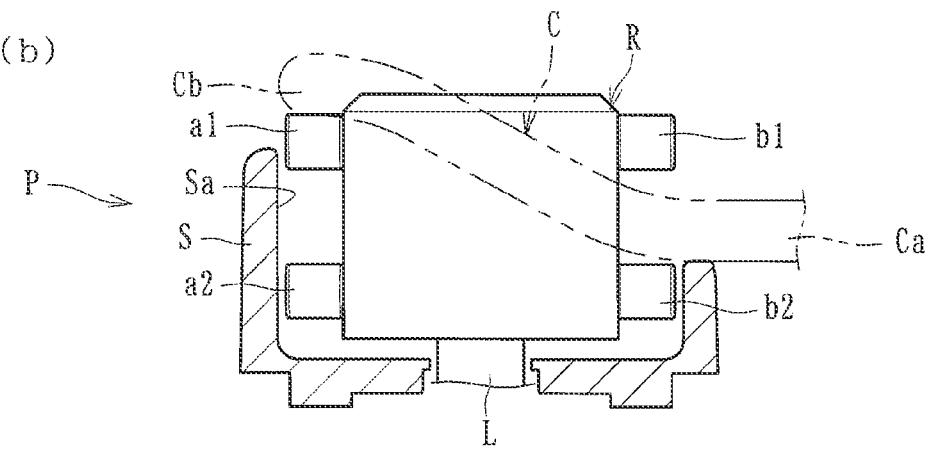
(c)
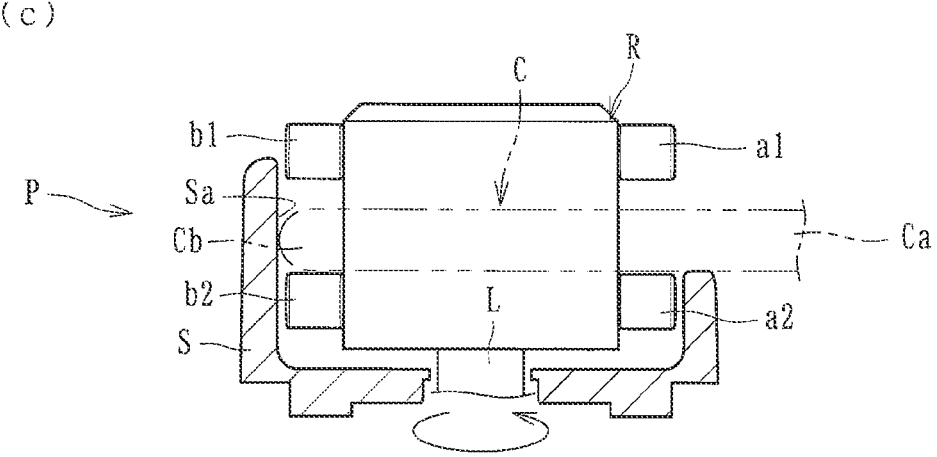

[Fig. 6]
(a)
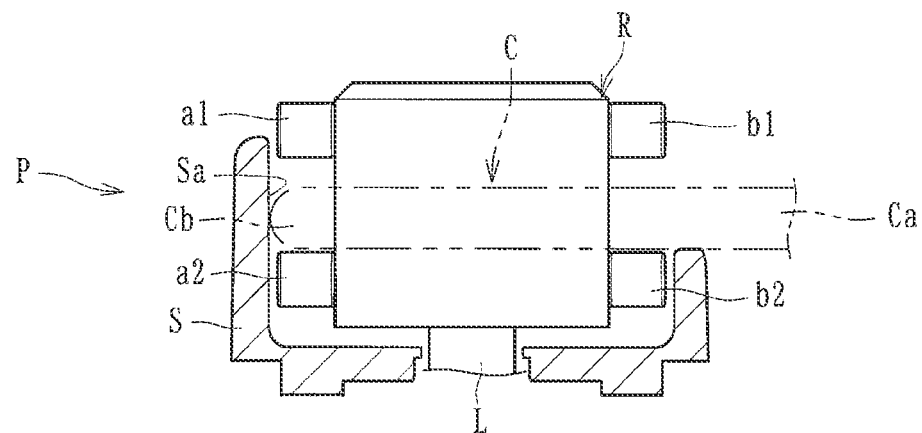
(b)
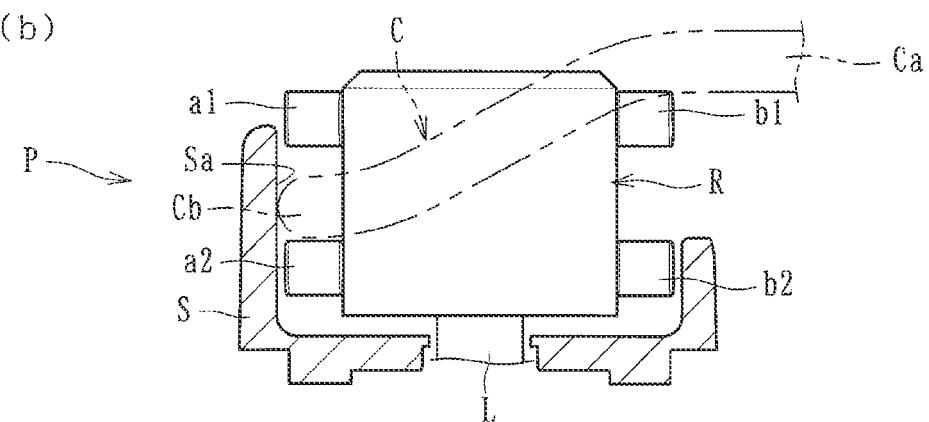
(c)
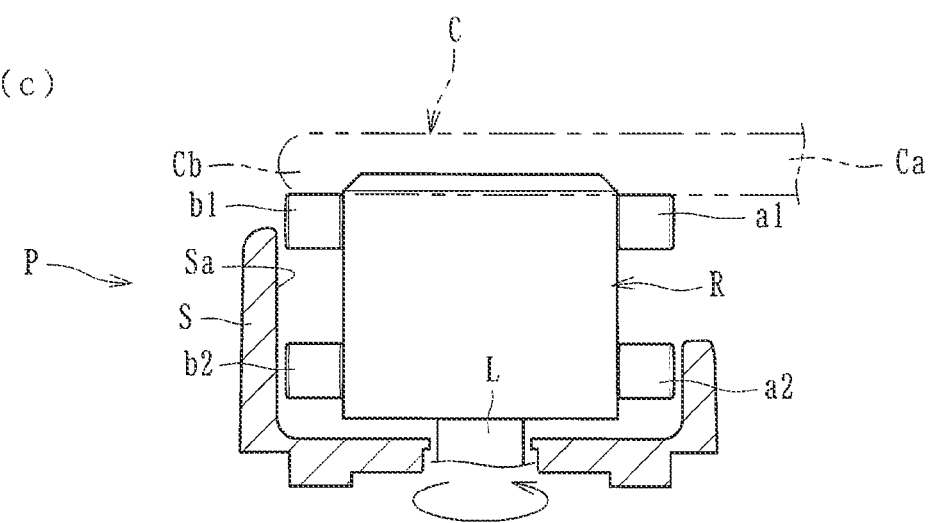

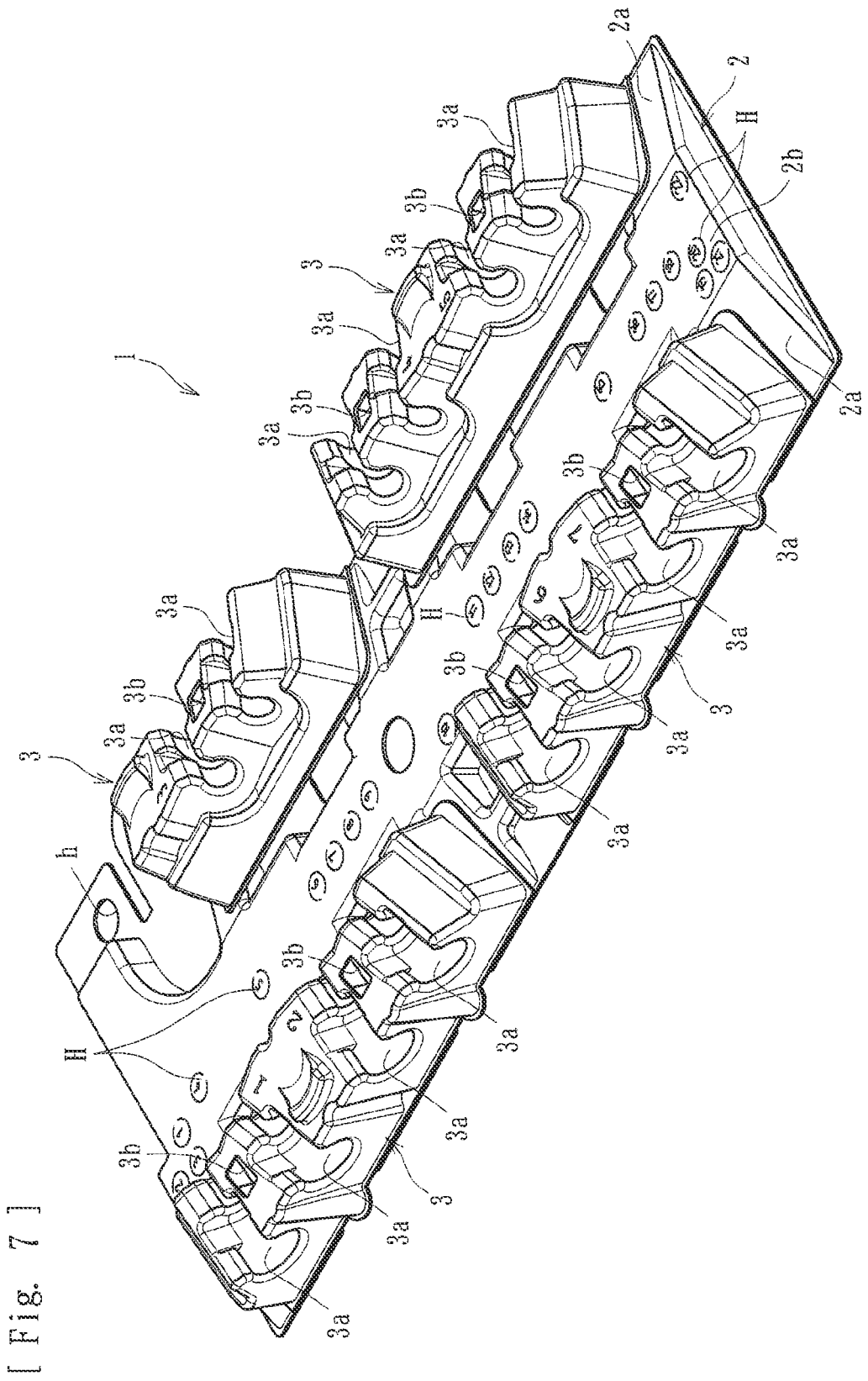
[Fig. 7]

[Fig. 8]
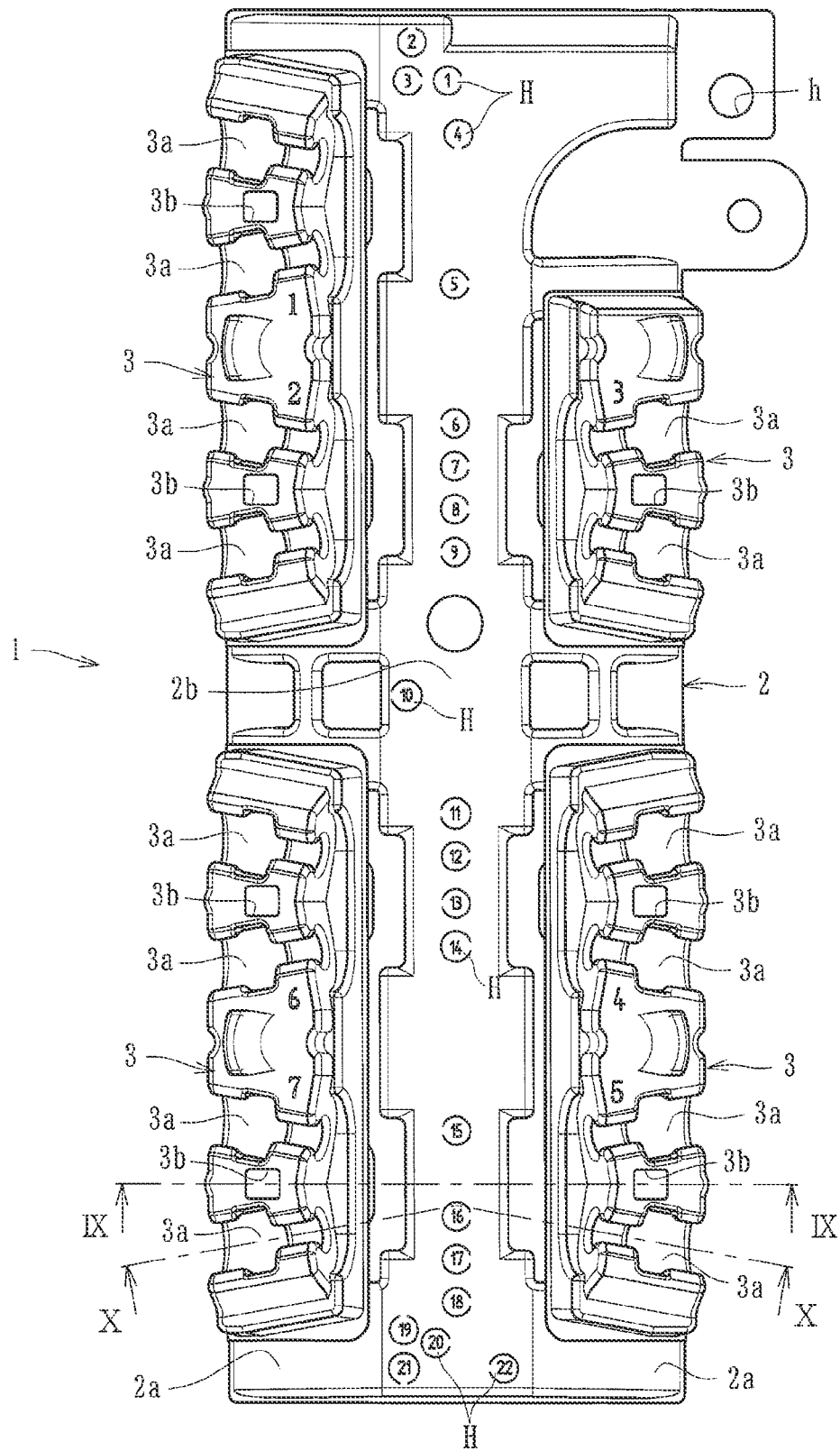

[Fig. 9]
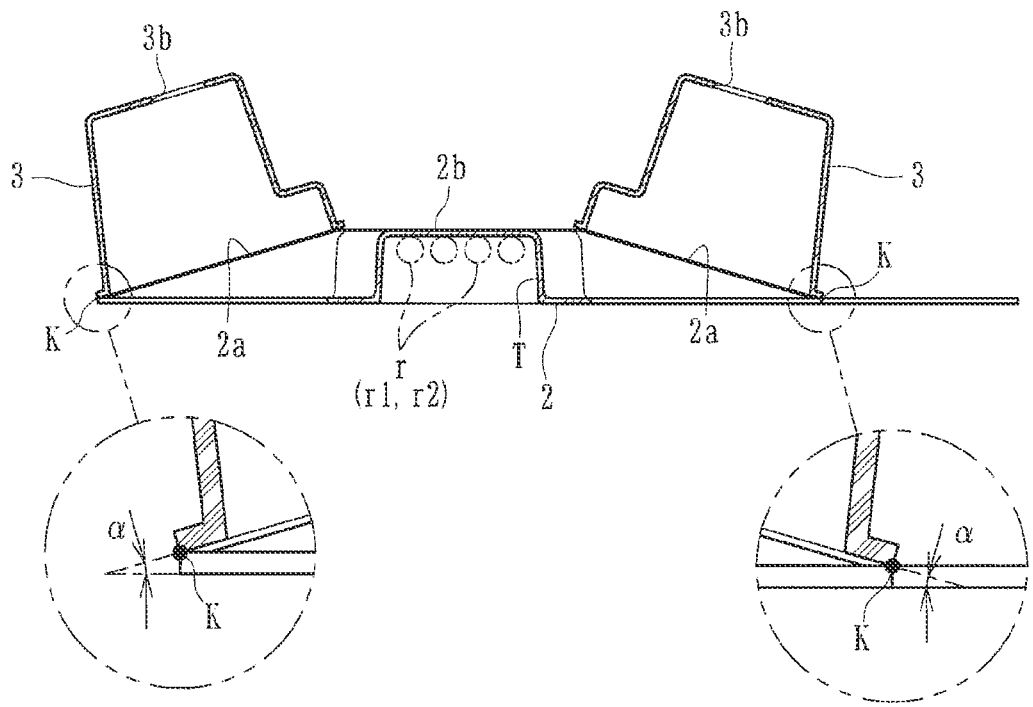
[Fig. 10]
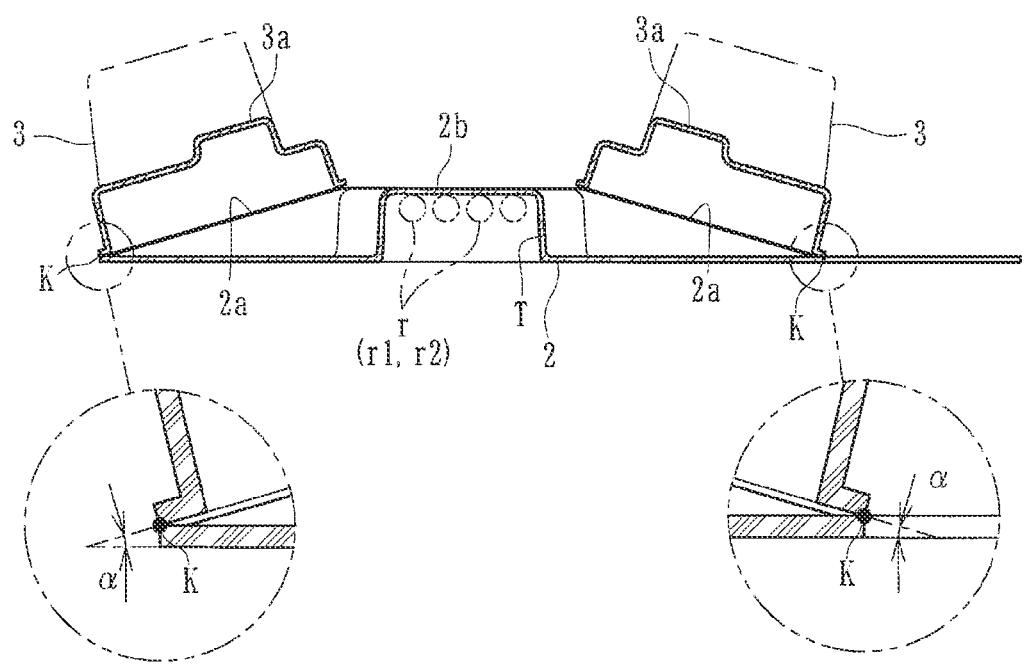

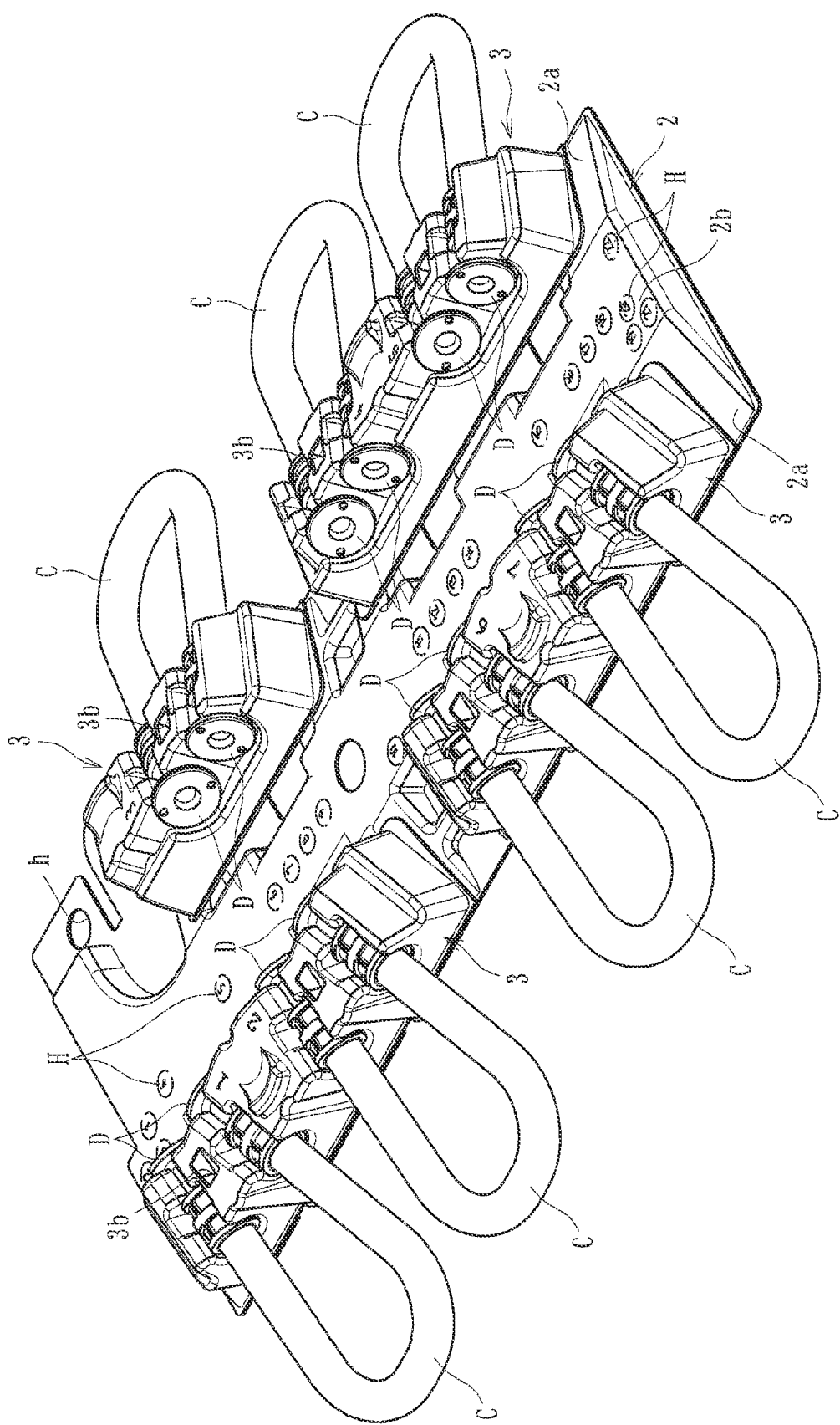
[Fig. 11]

[Fig. 12]
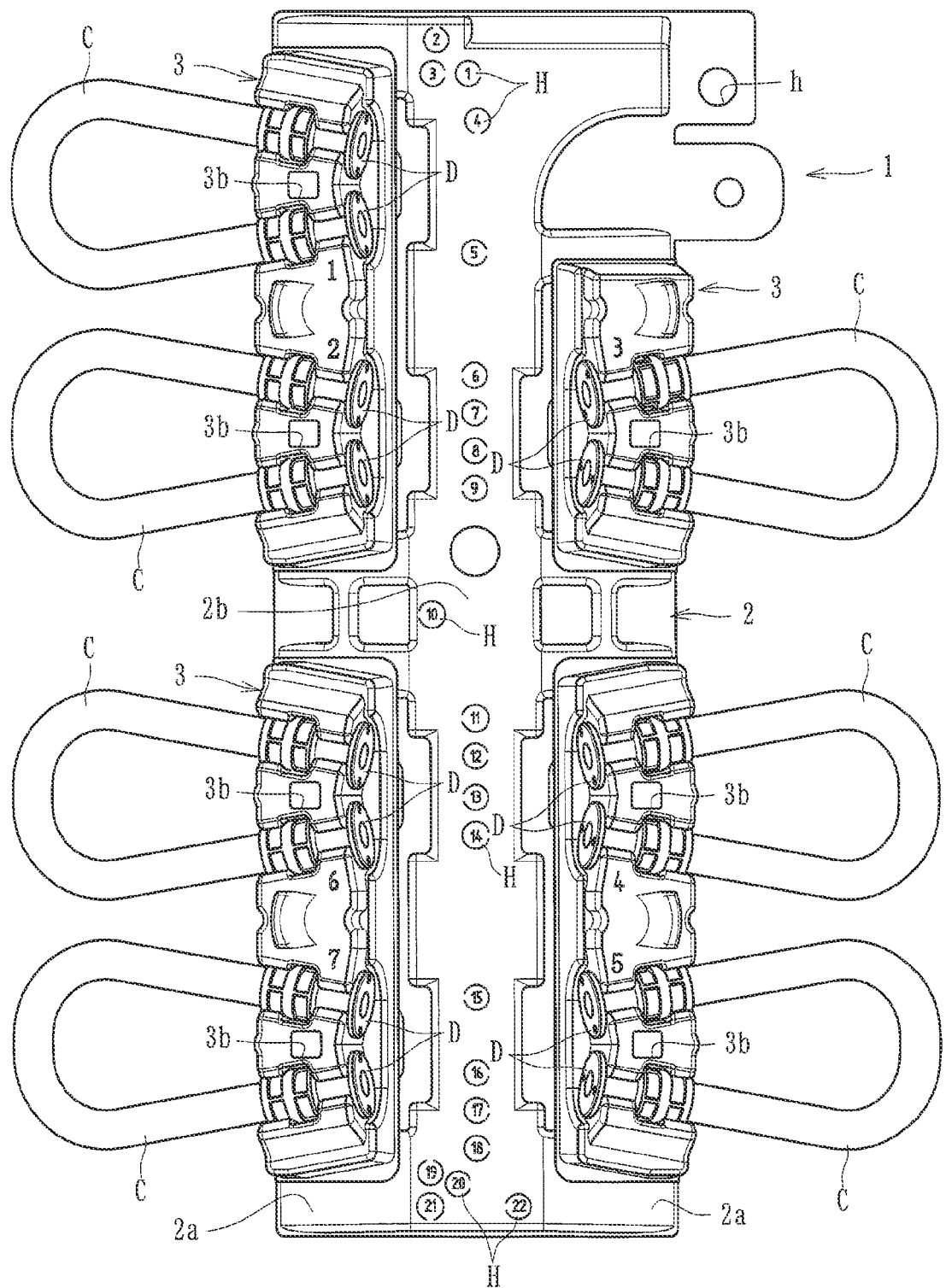

[Fig. 13]
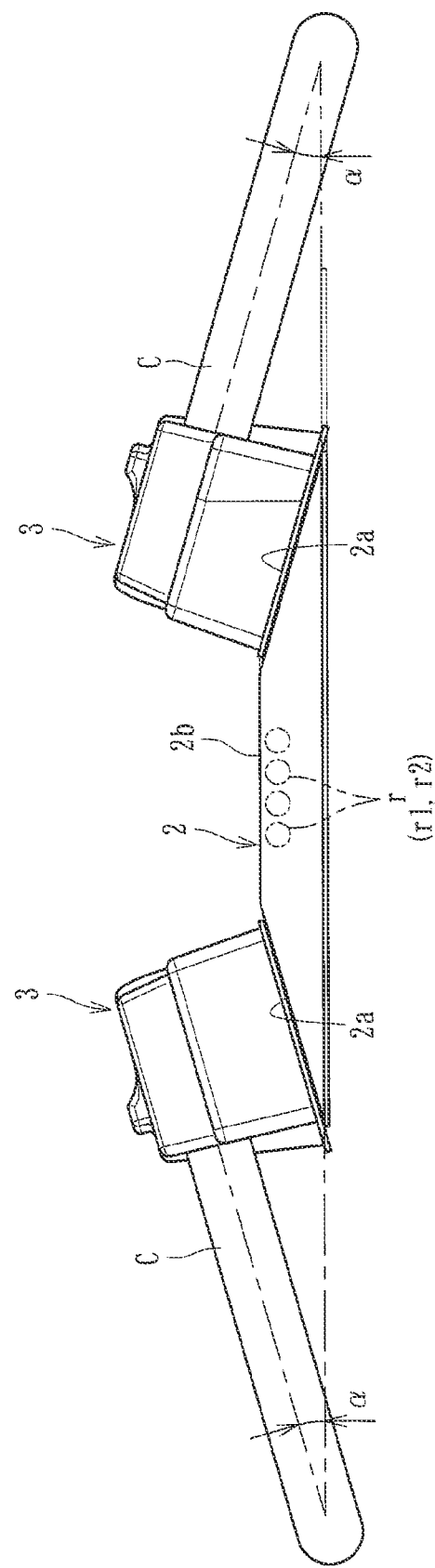

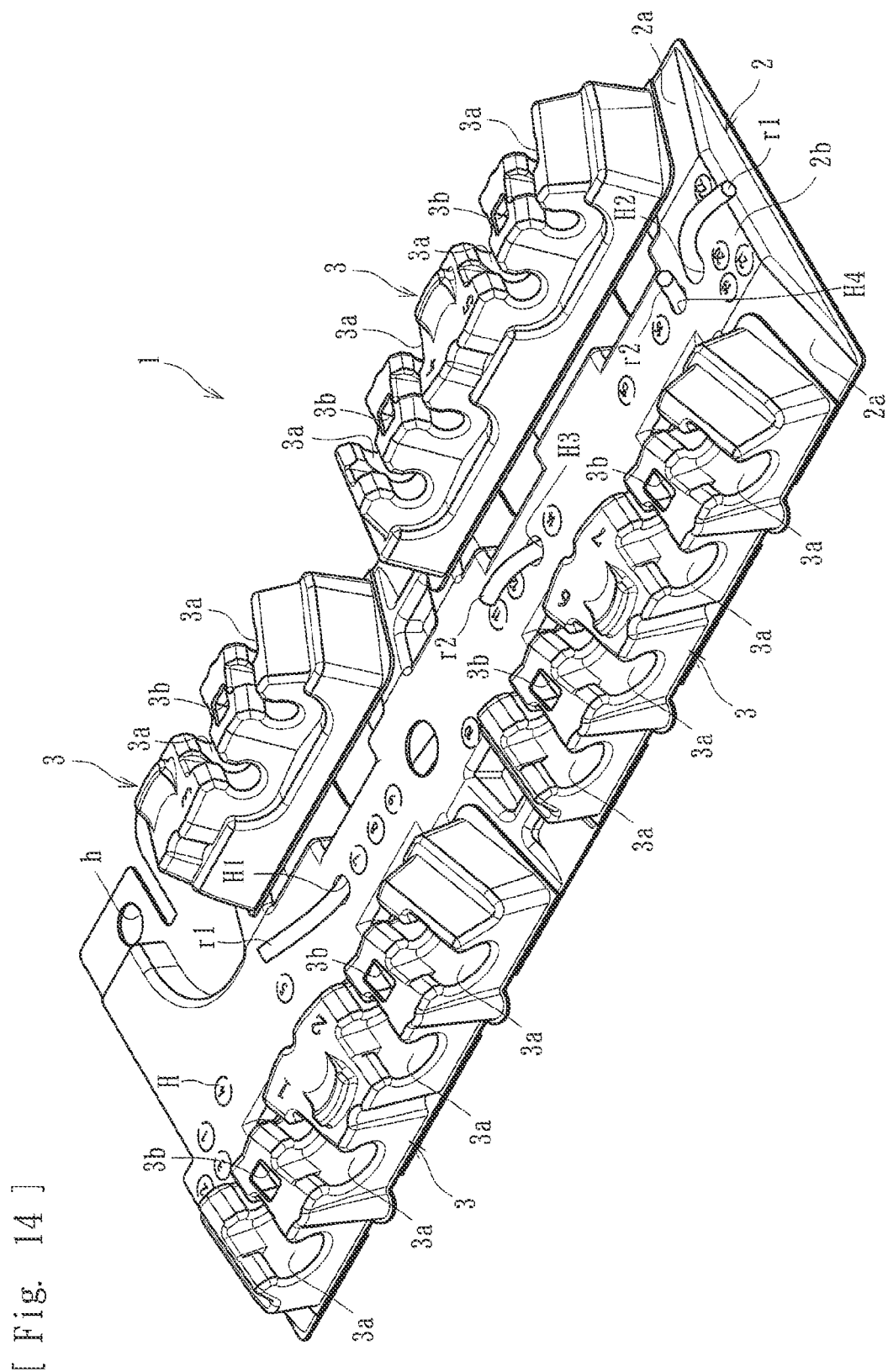
[Fig. 14]

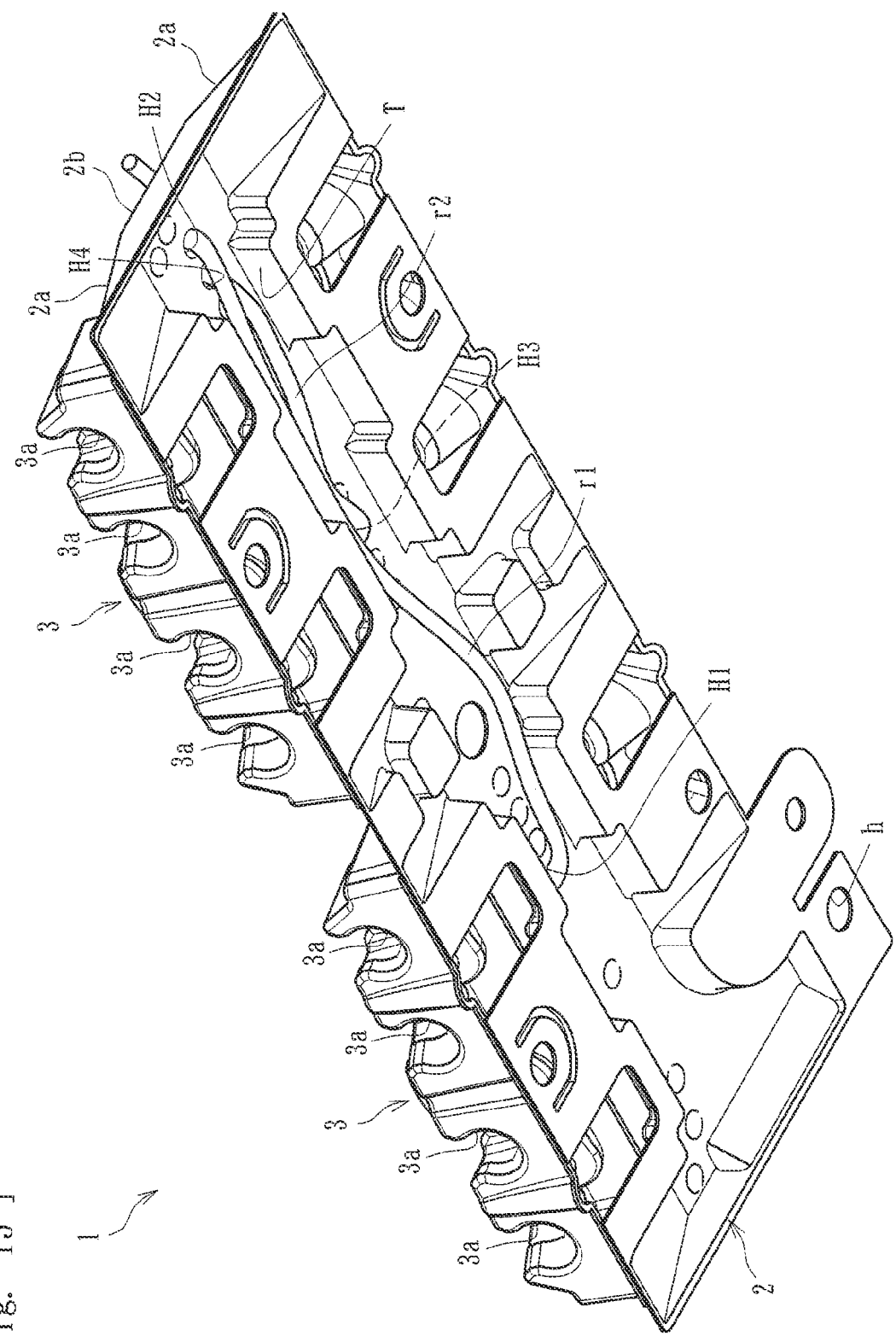
[Fig. 15]

[Fig. 16]
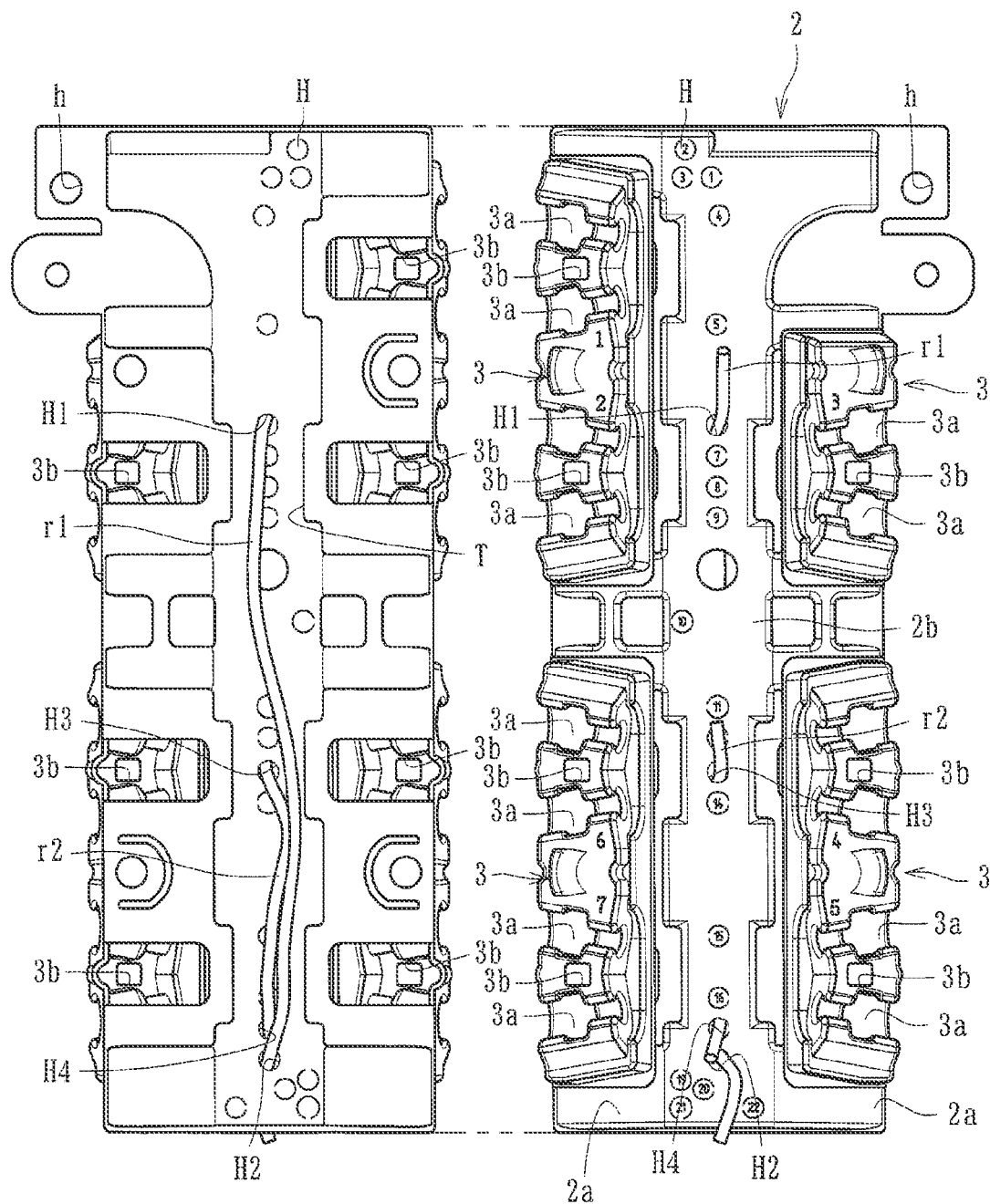

[Fig. 17]
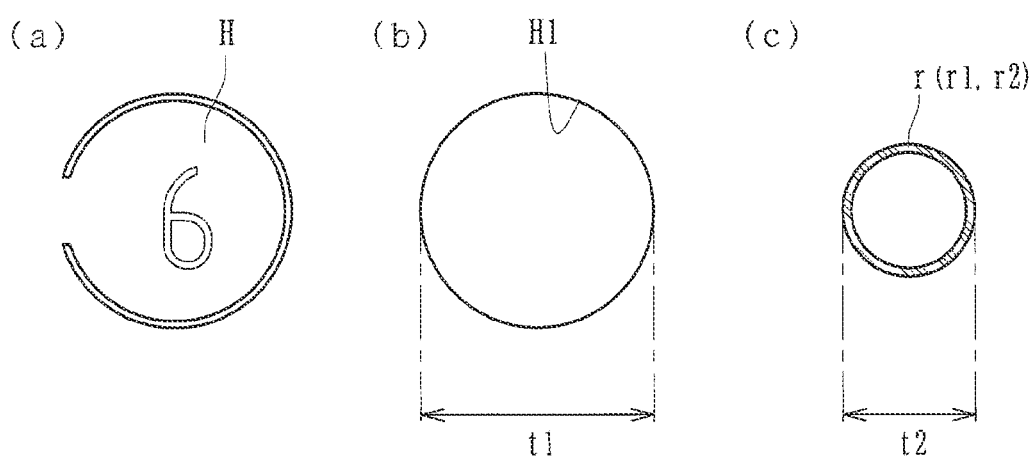

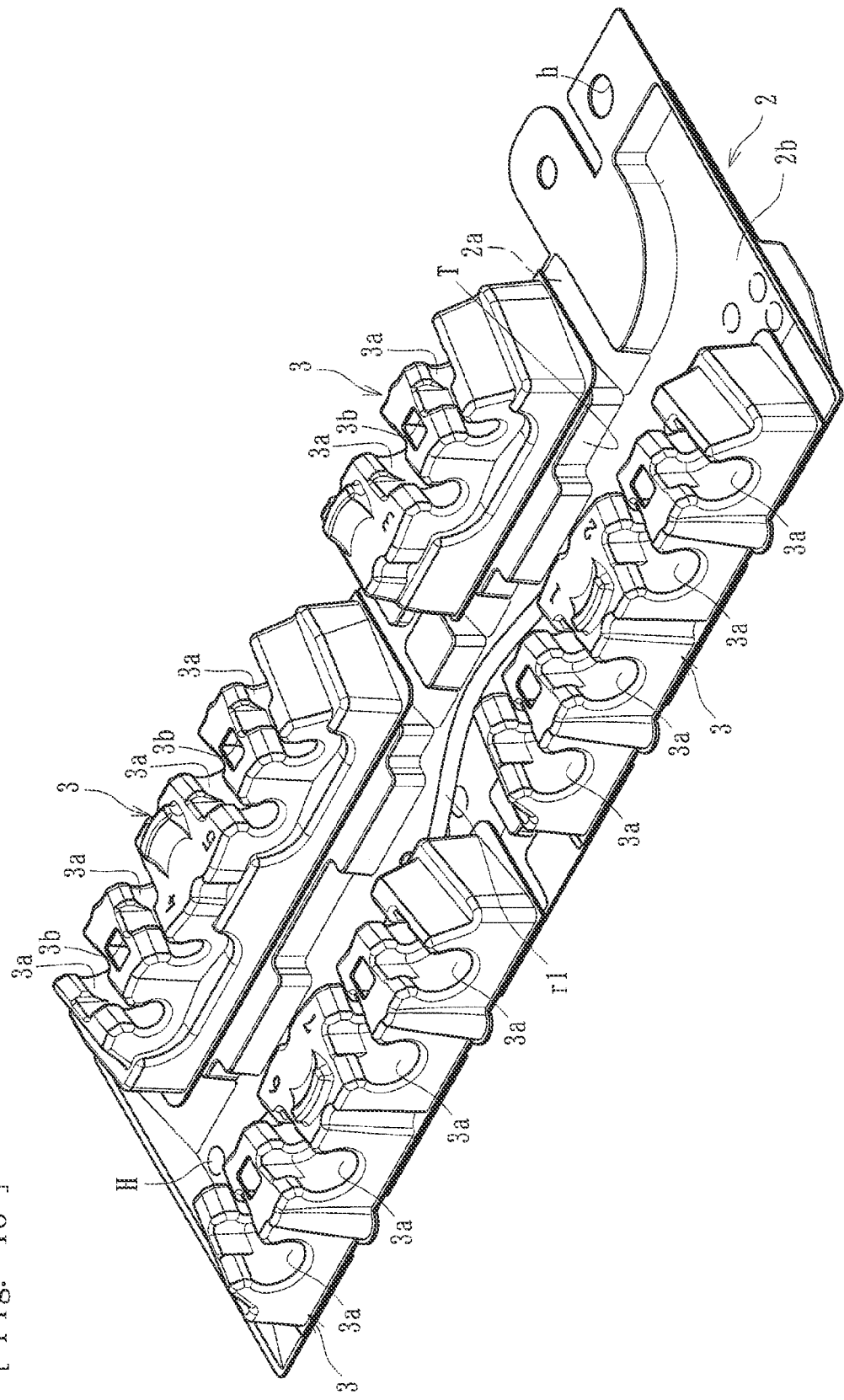
[Fig. 18]

[Fig. 19]
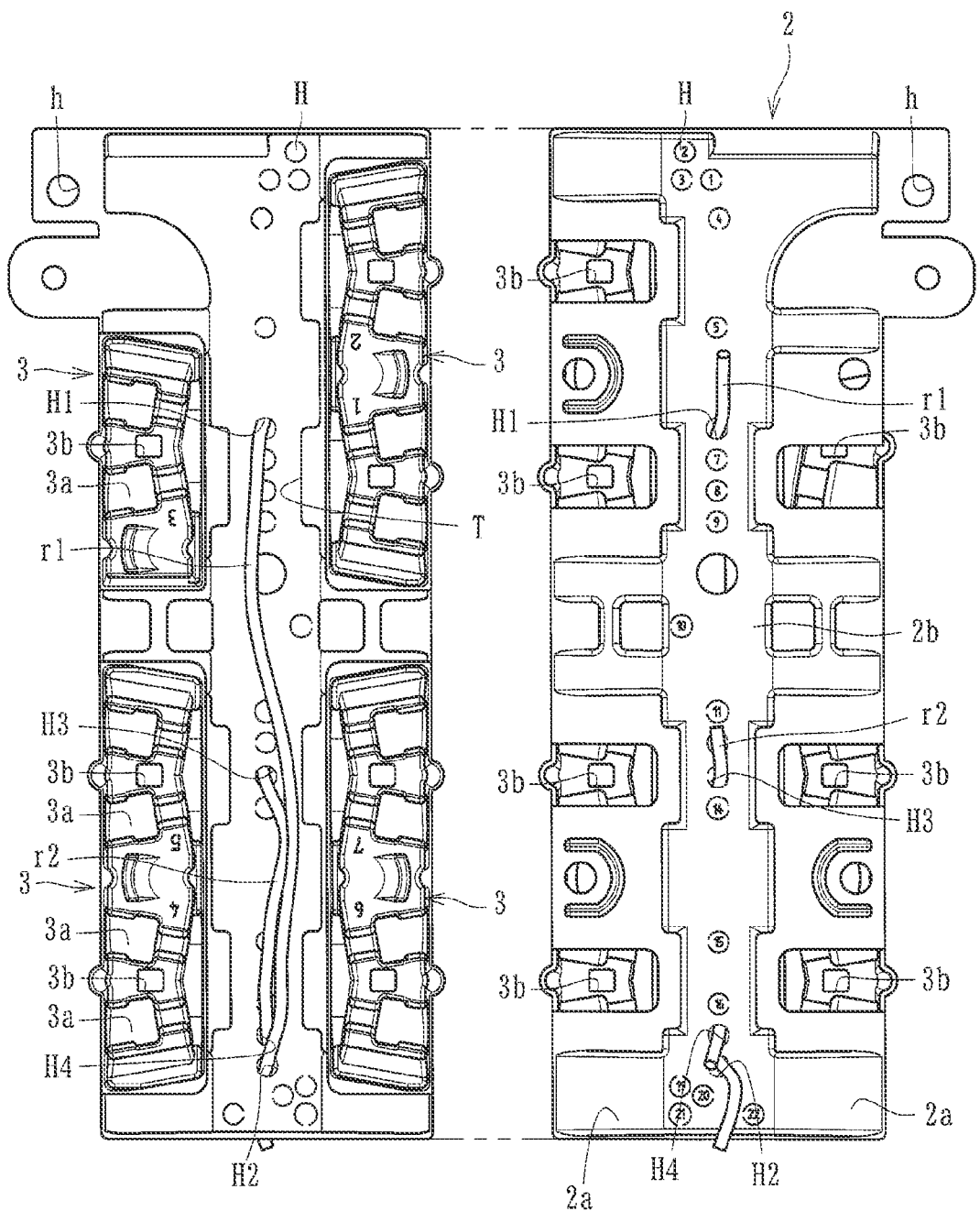

[Fig. 20]
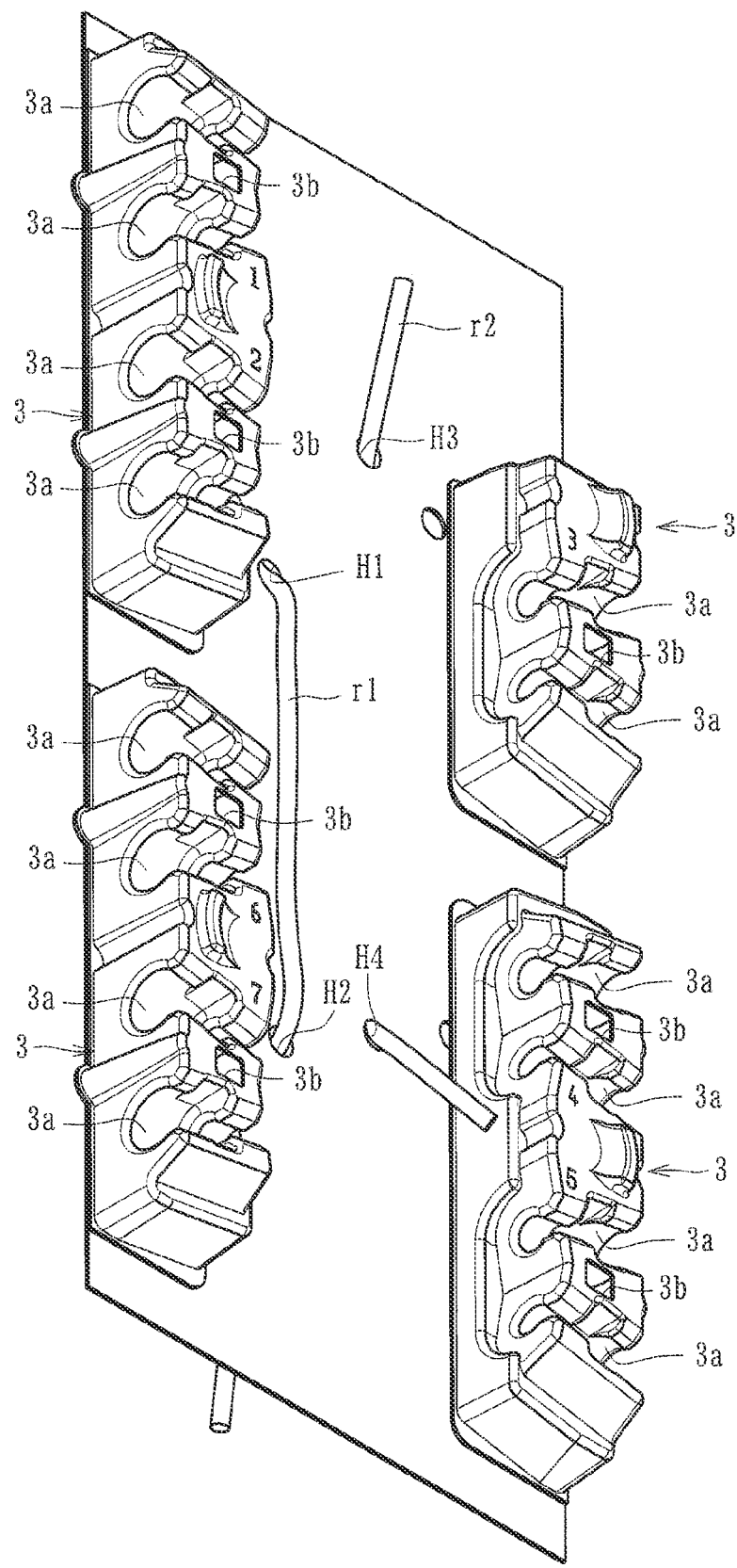

[Fig. 21]
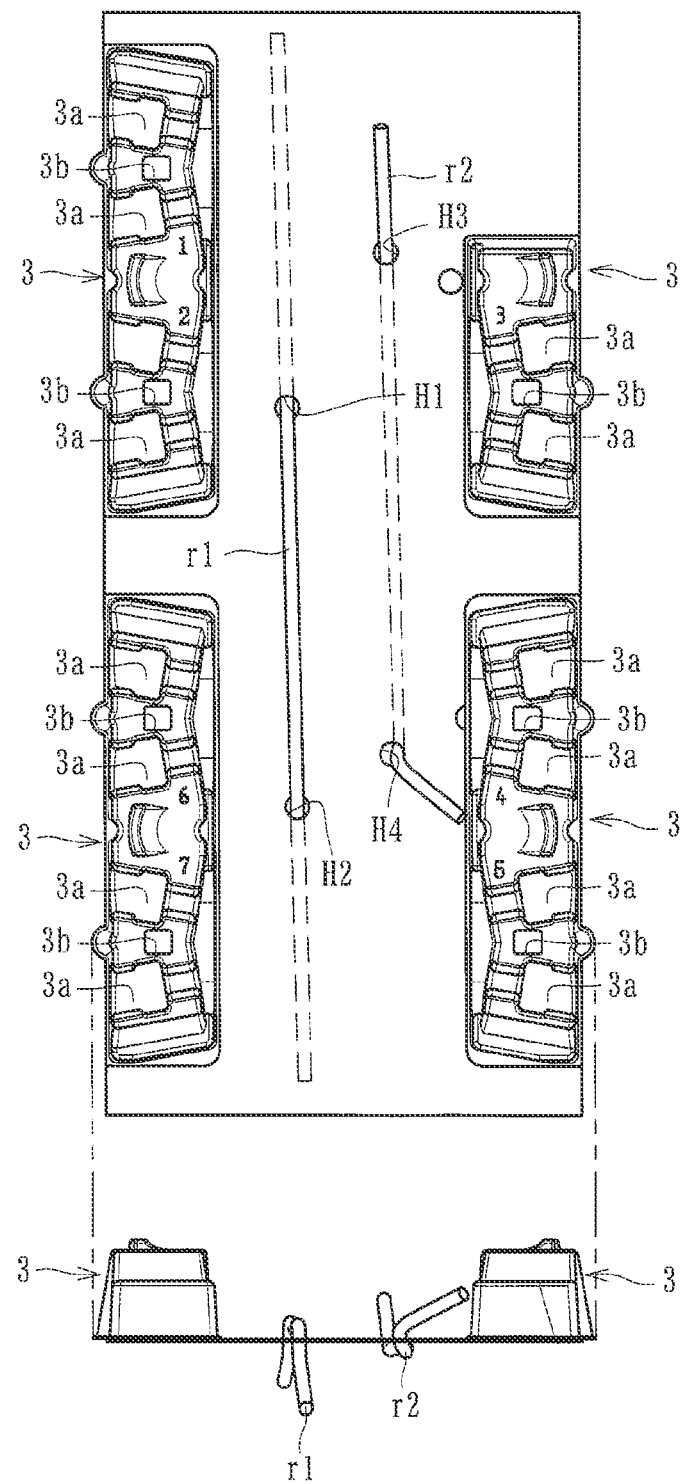

[Fig. 22]
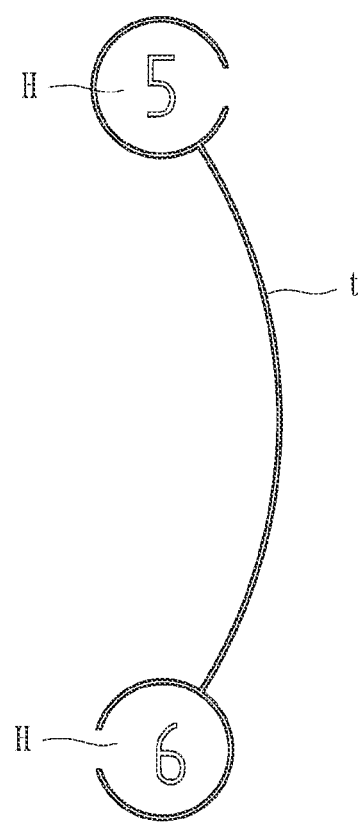

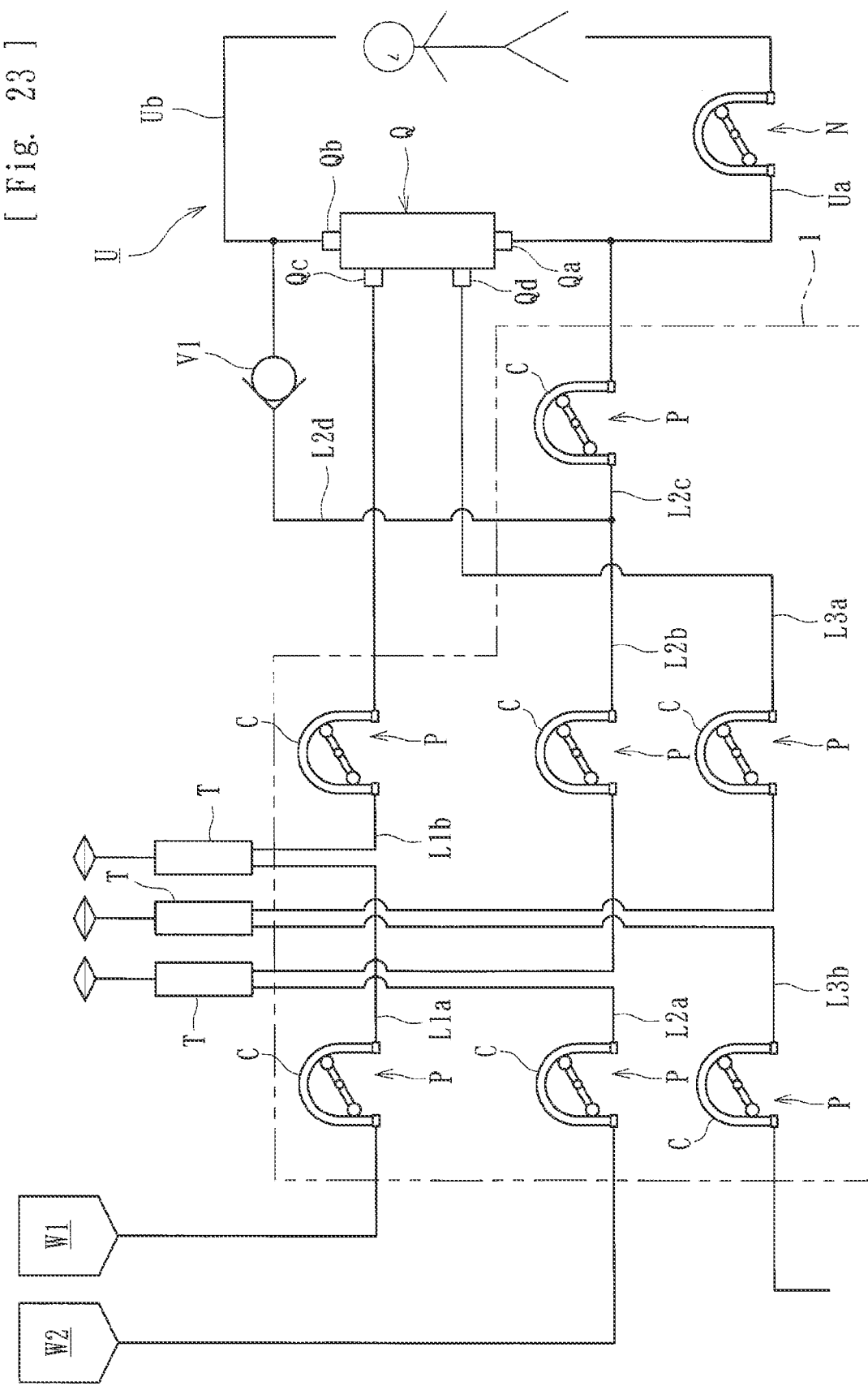
[Fig. 23]

ATTACHING MEMBER

CROSS-REFERENCE TO RELATED APPLICATION(S)

This application is a continuation of International Application No. PCT/JP2019/051339 filed on Dec. 26, 2019, which claims priority to Japanese Application No. 2018-246176, filed on Dec. 27, 2018, the entire disclosures of which are hereby incorporated by reference.

FIELD

The present teachings relate to an attaching member to be attached to a blood purification apparatus including peristaltic pumps, the attaching member holding pump tubes to be squeezed in a predetermined direction by the respective peristaltic pumps for liquid delivery.

BACKGROUND

In general, a blood purification apparatus for giving dialysis treatment is provided with an arterial blood circuit and a venous blood circuit that form a blood circuit for causing blood of a patient to extracorporeally circulate, a blood purifier for purifying the blood extracorporeally circulating through the blood circuit, and various treatment devices, such as a blood pump, for performing blood purification treatment with the blood circuit and the blood purifier. After the patient is punctured with an arterial puncture needle and a venous puncture needle, the blood pump is activated. Thus, blood of the patient flows through the arterial blood circuit and the venous blood circuit. In such a flowing process, the blood is purified by the blood purifier.

Some of blood purification apparatuses according to known proposals each include a plurality of peristaltic pumps for delivering liquids such as substitution fluid and drain liquid. The peristaltic pumps are provided with pump tubes, respectively, so that different liquids can be delivered. Hitherto, for example, an attaching member has been disclosed by PTL 1 that includes a plurality of pump tubes attachable to respective peristaltic pumps included in a blood purification apparatus. The attaching member is to be attached to a predetermined position of the blood purification apparatus.

PTL 1: Japanese Unexamined Patent Application Publication No. 2017-164285 the teachings of which are expressly incorporated by reference herein for all purposes.

SUMMARY

In the above known attaching member, however, not only a space for placing the pump tubes but also a space for placing other flexible tubes that each allow liquid to flow through is limited. Such a situation leads to a problem of complicated arrangement of the flexible tubes or an increase in the size of the body for securing an enough space for the flexible tubes.

The present teachings have been conceived in view of the above circumstances and provides an attaching member with which the arrangement of flexible tubes can be prevented from becoming complicated, and simultaneously a limited space can be used efficiently.

Variation 1 may comprise an attaching member to be attached to a blood purification apparatus including peristaltic pumps, the attaching member holding pump tubes to be squeezed in a predetermined direction by the respective peristaltic pumps for liquid delivery. The attaching member includes a body attachable to a predetermined position of the blood purification apparatus, and holding portions attached to the body and that hold the pump tubes. The holding portions are attached to edge portions on two opposite sides of the body, and flexible tubes that each allow liquid to flow through are to be placed in a central portion of the body, the central portion being positioned between the holding portion on one of the edge portions and the holding portion on the other of the edge portions.

According to variation 2, in the attaching member according to variation 1, may comprise the central portion has a recess that is open on a rear side in such a manner as to receive the flexible tubes, with a front side of the central portion covering the flexible tubes. According to the variation 3, in the attaching member according to variation 2, may comprise the body is transparent in at least the central portion.

According to variation 4, in the attaching member according to variation 1, may comprise the central portion has a recess that is open on a front side in such a manner as to receive the flexible tubes, with a rear side of the central portion covering the flexible tubes.

According to variation 5, in the attaching member according to any of variations 1 to 4, the central portion has securing parts where the flexible tubes are to be secured.

According to variation 6, in the attaching member according to any of variations 1 to 5, the securing parts are openings through which the flexible tubes are allowed to pass, and the flexible tubes are securable by being passed through the openings.

According to variation 7, there is provided a blood purification circuit connected to one of the pump tubes according to any of variations 1 to 6. The blood purification circuit includes a blood circuit through which blood is caused to extracorporeally circulate, and a flow route through which substitution fluid is introduced into the blood circuit or a flow route through which dialysate is introduced into a blood purifier connected to the blood circuit or drain liquid is discharged from the blood purifier.

According to variation 1, the holding portions are attached to the edge portions on the two opposite sides of the body, and the flexible tubes that each allow the liquid to flow through are to be placed in the central portion of the body, the central portion being positioned between the holding portion on one of the edge portions and the holding portion on the other of the edge portions. Therefore, the arrangement of the flexible tubes can be prevented from becoming complicated, and the limited space can be used efficiently.

According to variation 2, the central portion has the recess that is open on the rear side in such a manner as to receive the flexible tubes, with the front side of the central portion covering the flexible tubes. Therefore, the flexible tubes can be placed in the recess. Furthermore, since the flexible tubes are covered by the central portion on the front side, interference between the flexible tubes and other devices or the like can be prevented.

According to variation 3, the body is transparent in at least the central portion. Therefore, in addition to the prevention of interference between the flexible tubes covered by the central portion and other devices or the like, visual checking of the presence/absence of liquids in the flexible tubes can be facilitated through the transparent central portion.

According to variation 4, the central portion has the recess that is open on the front side in such a manner as to receive the flexible tubes, with the rear side of the central portion covering the flexible tubes. Therefore, the flexible tubes can be placed in the recess. Furthermore, the flexible tubes placed in the central portion can be visually checked directly.

According to variation 5, the central portion has the securing parts where the flexible tubes are to be secured. Therefore, the flexible tubes can be placed assuredly within the area defined as the central portion. Consequently, accidental displacement of the flexible tubes placed in the central portion to another area can be prevented.

According to variation 6, the securing parts are the openings through which the flexible tubes are allowed to pass, and the flexible tubes are securable by being passed through the openings. Therefore, the flexible tubes can be placed assuredly within the area defined as the central portion. Moreover, no space is necessary for securing the flexible tubes. Consequently, the increase in the size of the body can be avoided.

According to variation 7, a blood purification circuit that produces the advantageous effects according to variations 1 to 6 can be provided.

BRIEF DESCRIPTION OF THE DRAWINGS

FIG. 1 is an overall diagram of a blood purification apparatus, with an attaching member according to an embodiment of the present teachings attached thereto.

FIG. 2 is an overall diagram of the blood purification apparatus, with the attaching member yet to be attached thereto.

FIG. 3 is an enlargement of peristaltic pumps, with pump tubes of the attaching member yet to be attached thereto.

FIG. 4 is an enlargement of a part of the blood purification apparatus, with the attaching member anchored thereto.

FIG. 5 illustrates a process of attaching the pump tube to the peristaltic pump of the blood purification apparatus, including diagram (a) illustrating a state before an anchor member is moved, diagram (b) illustrating a state after the anchor member is moved but before loading is complete, and diagram (c) illustrating a state after loading is complete.

FIG. 6 illustrates a process of detaching the pump tube from the peristaltic pump of the blood purification apparatus, including diagram (a) illustrating a state before the anchor member is moved, diagram (b) illustrating a state after the anchor member is moved but before unloading is complete, and diagram (c) illustrating a state after unloading is complete.

FIG. 7 is a perspective view of the attaching member according to the present embodiment.

FIG. 8 is a front view of the attaching member.

FIG. 9 is a sectional view taken along line IX-IX illustrated in FIG. 8.

FIG. 10 is a sectional view taken along line X-X illustrated in FIG. 8.

FIG. 11 is a perspective view of the attaching member, with holding portions thereof holding pump tubes.

FIG. 12 is a front view of the attaching member holding the pump tubes.

FIG. 13 is a side view of the attaching member holding the pump tubes.

FIG. 14 is a front perspective view of the attaching member, with flexible tubes secured thereto by being passed through openings provided therein.

FIG. 15 is a rear perspective view of the attaching member, with the flexible tubes secured thereto by being passed through the openings provided therein.

FIG. 16 is a second-angle projection of the attaching member, with the flexible tubes secured thereto by being passed through the openings provided therein.

FIG. 17 includes diagrams illustrating sections of (a) a lid and (b) the opening of the attaching member, and (c) the flexible tube.

FIG. 18 is a perspective view of an attaching member according to another embodiment of the present teachings.

FIG. 19 is a second-angle projection of the attaching member.

FIG. 20 is a perspective view of an attaching member according to yet another embodiment of the present teachings.

FIG. 21 is a second-angle projection of the attaching member.

FIG. 22 is a plan view illustrating yet another embodiment of the present teachings.

FIG. 23 is a diagram of a blood purification apparatus with the attaching member attached thereto, and is provided for describing blood purification treatment.

DETAILED DESCRIPTION

Embodiments of the present teachings will now be described specifically with reference to the drawings.

An attaching member according to an embodiment is to be attached to a blood purification apparatus including peristaltic pumps. The attaching member holds pump tubes to be squeezed in a predetermined direction by the respective peristaltic pumps for liquid delivery. As illustrated in FIGS. 1 to 13, the attaching member includes a body 2 attachable to a predetermined position Ba of a blood purification apparatus B, and holding portions 3 attached to the body 2 and that hold pump tubes C.

As illustrated in FIGS. 7 to 16, the attaching member 1 is a resin molded component in which the body 2 and the holding portions 3 are formed continuously with each other. When the component is folded at folds K extending along the boundaries between the body 2 and the holding portions 3, the holding portions 3 are placed on the front face of the body 2 as illustrated in FIG. 7. The folds K each have perforations or the like. Therefore, the holding portions 3 are easily foldable with respect to the body 2.

As illustrated in FIGS. 7 to 13, the body 2 according to the present embodiment is a rectangular resin molded part and has inclined surfaces 2a (edge portions) provided on two opposite sides thereof, respectively. The inclined surfaces 2a are each inclined at a predetermined angle α with respect to the bottom surface of the body 2 (an attaching surface that faces the predetermined position Ba). Furthermore, the body 2 includes a central portion 2b positioned in the center thereof and between the left and right inclined surfaces 2a. Specifically, the body 2 has the central portion 2b in the center thereof, with the inclined surfaces 2a at the angle α extending from the central portion 2b toward the left and right sides, respectively. The inclined surfaces 2a carry a plurality of (four in the present embodiment) holding portions 3.

The holding portions 3 are each a resin molded part projecting in a block-like shape from the body 2 (projecting frontward). As illustrated in FIGS. 11 and 12, the holding portions 3 have holding grooves 3a, into each of which one of connectors D provided at two respective ends of each of the pump tubes C is to be fitted, whereby the connectors D are securable at a predetermined height. In short, the connectors D are secured by being fitted into the holding grooves 3a, whereby the pump tubes C are held by the holding portions 3 as illustrated in FIGS. 11 to 13. Furthermore, as illustrated in FIG. 9, the holding portions 3 have anchoring holes 3b (anchoring parts) in predetermined areas thereof and are therefore anchorable by anchor members A included in the blood purification apparatus B.

The pump tubes C are each made of a material such as soft resin or rubber forming a flow route with a relatively large diameter. Each pump tube C has the connectors D at one end and the other end thereof, respectively. After the pump tubes C are fitted into respective stators S of the peristaltic pumps P, respective rotors R are driven to rotate. Thus, the pump tubes C are squeezed in the lengthwise direction by rollers Ra, so that liquids such as substitution fluid and drain liquid can be delivered.

As illustrated in FIGS. 9, 10, and 13, the holding portions 3 according to the present embodiment are provided on the inclined surfaces 2a. Therefore, the pump tubes C each extend at the predetermined angle α (inclined along the inclined surface 2a) with respect to the bottom surface of the body 2 (the attaching surface that faces the predetermined position Ba). In other words, the holding portions 3 according to the present embodiment hold the connectors D of the pump tubes C in an inclined state. Specifically, the holding portions 3 hold the pump tubes C such that the pump tubes C are inclined in a direction in which the pump tubes C are fitted to the peristaltic pumps P (a downward direction in FIG. 13).

The body 2 according to the present embodiment is configured as follows. The holding portions 3 are attached to the edge portions (inclined surfaces 2a) on the two opposite sides of the body 2. Flexible tubes (r) that allow liquids to flow through are placed in the central portion 2b positioned between the holding portions 3 on one of the edge portions (inclined surfaces 2a) and the holding portions 3 on the other of the edge portions (inclined surfaces 2a). The flexible tubes (r) placed in the central portion 2b are either flexible tubes connected to the connectors D of the pump tubes C or flexible tubes extending from other devices.

As illustrated in FIGS. 15 and 16, the central portion 2b of the body 2 according to the present embodiment has a recess T that is open on the rear side (the side as the attaching surface facing the blood purification apparatus B) in such a manner as to receive the flexible tubes (r), with the front side (the side opposite the attaching surface) thereof covering the flexible tubes (r). In other words, the central portion 2b of the body 2 according to the present embodiment has the recess T (a concavity) that is open on the rear side. In front view, the flexible tubes (r) are hidden. The flexible tubes (r) (such as tubes connected to the connectors D of the pump tubes C) are received in such a manner as to run along the recess T that is open on the rear side. It is preferable that the body 2 be transparent in at least the central portion 2b thereof so that the flexible tubes (r) behind the central portion 2b are visible.

As illustrated in FIGS. 1 to 3, the blood purification apparatus B applied to the present embodiment is a monitoring apparatus for hemodialysis treatment that includes a monitor M capable of displaying information regarding blood purification treatment and the like, a blood pump N, and so forth. When the blood pump N is activated, blood of a patient is caused to extracorporeally circulate through a blood circuit. Meanwhile, the blood undergoes blood purification treatment in a blood purifier (a dialyzer). The blood purification apparatus B according to the present embodiment includes a plurality of (seven in the present embodiment) peristaltic pumps P provided on the front face thereof, so that substitution fluid and drain liquid can be delivered in the blood purification treatment.

The peristaltic pumps P are each capable of delivering liquid by squeezing the pump tube C in a specific direction and each include, as illustrated in FIGS. 3 to 6, the stator S having a fitting recess Sa, the rotor R provided in the fitting recess Sa and being rotatable about a rotating shaft L, and the rollers Ra provided on the rotor R. When the pump tube C is fitted into the fitting recess Sa of the stator S and the rotor R is driven to rotate, the pump tube C is squeezed between the wall of the fitting recess Sa and the rollers Ra. Thus, the liquid can be delivered.

The rotor R has an upper guide pin a1 and a lower guide pin a2 provided in a pair, and an upper guide pin b1 and a lower guide pin b2 provided in a pair, all of which project from the rotor R. The pump tube C is to be fitted between the upper guide pin a1 and the lower guide pin a2 and between the upper guide pin b1 and the lower guide pin b2. The upper guide pins a1 and b1 are positioned on the open side of the fitting recess Sa. The lower guide pins a2 and b2 are positioned on the bottom side of the fitting recess Sa. Thus, displacement of the pump tube C fitted in the fitting recess Sa from a predetermined position (a position where the pump tube C is squeezable by the rollers Ra) is suppressed.

The blood purification apparatus B according to the present embodiment receives the attaching member 1 attachable to the predetermined position Ba on the front face thereof, where the peristaltic pumps P are provided. Specifically, as illustrated in FIG. 4, the blood purification apparatus B according to the present embodiment has a positioning pin (g). When the positioning pin (g) is inserted into a positioning hole (h) provided in the body 2 of the attaching member 1, the attaching member 1 can be positioned at the predetermined position Ba of the blood purification apparatus B.

As illustrated in FIG. 2, the blood purification apparatus B according to the present embodiment further has a plurality of anchor members A at the predetermined position Ba. Meanwhile, as described above, the holding portions 3 have the anchoring holes 3b (the anchoring parts) at which the holding portions 3 are anchorable by the anchor members A. The anchor members A each include an anchor hook on one side of the distal end thereof, and a pushing portion on the other side. The anchor hook is hooked on the peripheral edge of the anchoring hole 3b. Thus, the attaching member 1 is anchored by the anchor member A and is secured to the predetermined position Ba.

In a state where the attaching member 1 is positioned by the positioning pin (g) and is anchored at the anchoring holes 3b (the anchoring parts) by the anchor hooks of the anchor members A, as illustrated in FIG. 5(a), proximal portions Ca and a distal portion Cb of each of the pump tubes C held by the holding portions 3 are positioned above the upper guide pins a1 and b1 of a corresponding one of the peristaltic pumps P. Meanwhile, the rotor R of each of the peristaltic pumps P is stopped at a predetermined position (see FIGS. 2 to 4). In such an anchoring state, the anchor member A is moved in such a direction as to sink into the predetermined position Ba (a direction in which the attaching member 1 is moved toward the predetermined position Ba). Then, as illustrated in FIG. 5(b), the proximal portions Ca of the pump tube C are positioned between the upper guide pin b1 and the lower guide pin b2, while the distal portion Cb of the pump tube C is positioned above the upper guide pin a1.

In such a state, the rotor R is driven to rotate. Then, as illustrated in FIG. 5(c), while the proximal portions Ca of the pump tube C are positioned between the upper guide pin a1 and the lower guide pin a2, the distal portion Cb of the pump tube C interferes with the upper guide pin b1 and is drawn to a position between the upper guide pin b1 and the lower guide pin b2. Thus, the pump tube C is set in the peristaltic pump P. Such attaching work of setting the pump tube C by drawing the pump tube C to the position between the upper guide pin a1 and the lower guide pin a2 is also referred to as loading.

On the other hand, in the state where the pump tube C is set in the peristaltic pump P as illustrated in FIG. 6(a) with the anchor member A anchoring at the anchoring hole 3b (the anchoring part), the anchor member A is moved in such a direction as to project (a direction in which the attaching member 1 is lifted from the predetermined position Ba). Then, the pushing portion of the anchor member A pushes the peripheral edge of the anchoring hole 3b and lifts the pump tube C from the fitting recess Sa. Meanwhile, the rotor R of each of the peristaltic pumps P is stopped at the same predetermined position (see FIGS. 2 to 4) as in the case of the loading of the pump tube. Furthermore, as illustrated in FIG. 6(b), the distal portion Cb of the pump tube C is positioned between the upper guide pin a1 and the lower guide pin a2, and the proximal portions Ca of the pump tube C are positioned above the upper guide pin b1.

In such a state, the rotor R is driven to rotate. Then, as illustrated in FIG. 6(c), while the proximal portions Ca of the pump tube C are positioned above the upper guide pin a1, the distal portion Cb of the pump tube C interferes with the upper guide pin b1 and is pushed to a position above the upper guide pin b1. Thus, the pump tube C that has been set in the peristaltic pump P is unset and is allowed to be detached. Such detaching work of unsetting the pump tube C by pushing out the pump tube C from the position between the upper guide pin a1 and the lower guide pin a2 is also referred to as unloading.

As illustrated in FIGS. 14 to 16, the central portion 2b of the body 2 according to the present embodiment has openings (H1 to H4) through which flexible tubes (r1 and r2) are allowed to pass. The flexible tube r1 is securable by being passed through the openings (H1 and H2). The flexible tube r2 is securable by being passed through the openings (H3 and H4). Specifically, the openings (H1 to H4) are provided in pairs (the opening H1 and the opening H2 are paired, and the opening H3 and the opening H4 are paired), the openings in each of the pairs being spaced apart from each other. The flexible tubes (r1 and r2) are each securable by being passed through a corresponding one of the pairs of openings (the openings H1 and H2, and the openings H3 and H4).

More specifically, the flexible tube r1 is made to pass through the opening H1 from the front side of the body 2 to the inside of the recess T provided on the rear side of the central portion 2b, run along the recess T, and pass through the opening H2 to the front side of the body 2. Thus, the flexible tube r1 is secured by being passed through the pair of openings (H1 and H2). Likewise, the flexible tube r2 is made to pass through the opening H3 from the front side of the body 2 to the inside of the recess T provided on the rear side of the central portion 2b, run along the recess T, and pass through the opening H4 to the front side of the body 2. Thus, the flexible tube r2 is secured by being passed through the pair of openings (H3 and H4).

In the present embodiment, as illustrated in FIG. 17(a), a plurality of lids H that cover the openings are provided, and the flexible tubes (r) are allowed to pass through the openings when the lids H are removed. For example, part of each lid H is connected to the central portion 2b of the body 2. When the lid H is pushed by a finger, the connected part is cut or folded, whereby the opening H1 (or any of H2 to H4) is obtained as illustrated in FIG. 17(b). Alternatively, the openings (H1 to H4) may be provided with no lids H, and the flexible tubes (r) may be passed through any of the openings (H1 to H4).

The openings (H1 to H4) may each have an inside diameter t1 (see FIG. 17(b)) that is smaller than an outside diameter t2 of a corresponding one of the flexible tubes (r). In such a case, the flexible tubes (r) are press-fitted into the openings (H1 to H4) when being passed therethrough. It is preferable that the inside diameter t1 of each of the openings (H1 to H4) be set in accordance with (the material, thickness, or the like of) a corresponding one of the flexible tubes (r) or the position where the flexible tube r is to be secured. In such a case, since the degree of press-fitting varies with the difference between the inside diameter t1 and the outside diameter t2, the force of holding the flexible tube r can be adjusted arbitrarily.

The central portion 2b of the body 2 according to the present embodiment has the recess T that is open on the rear side in such a manner as to receive the flexible tubes (r), with the front side (the side opposite the attaching surface) thereof covering the flexible tubes (r). Alternatively, as illustrated in FIGS. 18 and 19, the central portion 2b may have a recess T that is open on the front side in such a manner as to receive the flexible tubes (r), with the rear side thereof covering the flexible tubes (r). In such a case as well, the openings (H1 to H4) as securing parts are provided in the recess T provided in the central portion 2b, and the flexible tubes (r) received by the recess T are secured by being passed through the openings (H1 to H4).

As another alternative, as illustrated in FIGS. 20 and 21, the central portion 2b of the body 2 may form a flat surface with no recess T, and the flexible tubes (r) may be placed on the flat surface. In such a case as well, the openings (H1 to H4) as securing parts are provided in the flat central portion 2b, and the flexible tubes (r) are secured by being passed through the openings (H1 to H4).

In the present embodiment, the lids H are given respective marks by which the openings are identifiable. For example, the marks may be numbers provided on the lids H as in the present embodiment or may be any of various other symbols, characters, shapes, and colors that are usable as identifiers. Moreover, a configuration that enables the identification of which of the openings are occupied by the flexible tubes (r) may be employed. In such a case, which of the openings are to be used for receiving flexible tubes (r) can be set for each of different treatments.

When the attaching member 1 is anchored to the predetermined position Ba of the blood purification apparatus B and the pump tubes C are loaded onto the respective peristaltic pumps P, a treatment apparatus for blood purification treatment is established as illustrated in FIG. 23. The treatment apparatus includes a blood circuit U including a dialyzer Q; a first dialysate introduction line L1a and a second dialysate introduction line L1b through which dialysate is introduced into the dialyzer Q; a first substitution line L2a, a second substitution line L2b, a pre-substitution line L2c, and a post-substitution line L2d through which substitution fluid is supplied to the blood circuit U; and a first drain-liquid discharge line L3a and a second drain-liquid discharge line L3b through which drain liquid is discharged from the dialyzer Q.

The blood circuit U includes an arterial blood circuit Ua and a venous blood circuit Ub. When the blood pump N is activated while a patient is punctured with the distal ends of the arterial blood circuit Ua and the venous blood circuit Ub, blood of the patient can be caused to extracorporeally circulate. The dialyzer Q has a blood introduction port Qa, a blood delivery port Qb, a dialysate introduction port Qc, and a dialysate delivery port Qd all projecting from a housing thereof. The arterial blood circuit Ua is connected to the blood introduction port Qa. The venous blood circuit Ub is connected to the blood delivery port Qb. The second dialysate introduction line L1b is connected to the dialysate introduction port Qc. The first drain-liquid discharge line L3a is connected to the dialysate delivery port Qd.

The first dialysate introduction line L1a is connected to a dialysate bag W1 that stores dialysate and is also connected to the second dialysate introduction line L1b through a temporary chamber T. When the peristaltic pumps P provided to the first dialysate introduction line L1a and the second dialysate introduction line L1b are activated, the dialysate in the dialysate bag W1 is temporarily stored in the temporary chamber T and is then introduced into the dialyzer Q.

The first substitution L2a is connected to a substitution-fluid bag W2 that stores substitution fluid and is also connected to the second substitution line L2b through a temporary chamber T. The second substitution line L2b is connected to the blood circuit U through the pre-substitution line L2c connected to the arterial blood circuit Ua and through the post-substitution line L2d connected to the venous blood circuit Ub. The post-substitution line L2d is provided with a check valve V1. When the peristaltic pumps P provided to the first substitution line L2a and the second substitution line L2b are activated, the substitution fluid in the substitution-fluid bag W2 is temporarily stored in the temporary chamber T and is then introduced into the arterial blood circuit Ua or the venous blood circuit Ub in accordance with the state of operation of the peristaltic pump P provided to the pre-substitution line L2c.

The first drain-liquid discharge line L3a is connected to the dialyzer Q and is also connected to the second drain-liquid discharge line L3b through a temporary chamber T. The second drain-liquid discharge line L3b allows the drain liquid to be discharged therethrough to the outside of the apparatus. When the peristaltic pumps P provided to the first drain-liquid discharge line L3a and the second drain-liquid discharge line L3b are activated, the drain liquid in the dialyzer Q is temporarily stored in the temporary chamber T and is then allowed to be discharged to the outside of the apparatus.

As described above, the pump tubes C of the attaching member 1 are connected to the flow routes (the first substitution line L2a, the second substitution line L2b, and the pre-substitution line L2c) through which the substitution fluid is introduced into the blood circuit U, the flow routes (the first dialysate introduction line L1a and the second dialysate introduction line L1b) through which the dialysate is introduced into the dialyzer Q (a blood purifier) connected to the blood circuit U, and the flow routes (the first drain-liquid discharge line L3a and the second drain-liquid discharge line L3b) through which the drain liquid is discharged from the dialyzer Q (the blood purifier). The post-substitution line L2d may also be connected to one of the pump tubes C of the attaching member 1.

In the present embodiment, none of the pump tubes C of the attaching member 1 is attached to the blood pump N. Alternatively, one of the pump tubes C of the attaching member 1 may be attached to the blood pump N by loading the pump tube C thereon. In such a case, what is to be connected to the pump tube C of the attaching member 1 is the blood circuit U. That is, devices that are loadable onto the pump tubes C of the attaching member 1 according to the present teachings include a blood purification circuit that includes the following: the blood circuit U through which the blood is caused to extracorporeally circulate; and the flow routes (the first substitution line L2a, the second substitution line L2b, and the pre-substitution line L2c (or the post-substitution line L2d)) through which the substitution fluid is introduced into the blood circuit U, the flow routes (the first dialysate introduction line L1a and the second dialysate introduction line L1b) through which the dialysate is introduced into the dialyzer Q (the blood purifier) connected to the blood circuit U, or the flow routes (the first drain-liquid discharge line L3a and the second drain-liquid discharge line L3b) through which the drain liquid is discharged from the dialyzer Q (the blood purifier).

According to the above embodiment, the body 2 has the openings (H1 to H4) through which the flexible tubes (r1 and r2) that allow liquids to flow through are allowed to pass. Furthermore, the flexible tubes (r1 and r2) are securable by being passed through the openings (H1 to H4). Therefore, the flexible tubes (r1 and r2) can be secured assuredly with efficient use of a limited space. The openings (H1 to H4) may each have an inside diameter t1 that is smaller than the outside diameter t2 of a corresponding one of the flexible tubes (r1 and r2). In such a case, the flexible tubes (r1 and r2) can be secured firmly by being press-fitted into the openings (H1 to H4). Therefore, the flexible tubes (r1 and r2) can be secured more assuredly with efficient use of the limited space. The inside diameter t1 of each of the openings (H1 to H4) may be set in accordance with a corresponding one of the flexible tubes (r1 and r2) or the position where the flexible tube (r1 or r2) is to be secured. In such a case, the force of holding the flexible tube (r1 or r2) can be adjusted arbitrarily. That is, the flexible tube (r1 or r2) can be secured with a holding force that accords with the flexible tube (r1 or r2) or the position where the flexible tube (r1 or r2) is to be secured.

The openings (H1 to H4) according to the present embodiment are provided in pairs, the openings in each of the pairs being spaced apart from each other. Furthermore, the flexible tubes (r1 and r2) are each securable by being passed through a corresponding one of the pairs of openings (H1 to H4). Therefore, each of the flexible tubes (r1 and r2) can be held at two positions and can thus be secured more assuredly.

The lids H that cover the openings (H1 to H4) are provided, and the flexible tubes (r1 and r2) are allowed to pass through the openings (H1 to H4) when the lids H are removed. Therefore, any of the lids H provided to the openings (H1 to H4) may be removed, so that selected ones of the openings (H1 to H4) can be opened for securing the flexible tubes (r1 and r2). Furthermore, marks by which the openings (H1 to H4) are identifiable are provided. Therefore, workers can visually recognize which of the openings (H1 to H4) are to be used for receiving the individual flexible tubes (r1 and r2). Consequently, the occurrence of a situation where the flexible tubes (r1 and r2) may be passed through wrong openings (H1 to H4) can be suppressed. If which of the openings (H1 to H4) are to be used for receiving the individual flexible tubes (r1 and r2) is set for each of different treatments, the setting can be changed easily. Consequently, the attaching member 1 can be used in different treatments easily.

If a configuration that enables the identification of which of the openings (H1 to H4) are occupied by the flexible tubes (r1 and r2) is employed, a situation where the flexible tubes (r1 and r2) have been passed through wrong openings (H1 to H4) can be recognized and notified of. Furthermore, if which of the openings (H1 to H4) are to be used for receiving the individual flexible tubes (r1 and r2) is set for each of different treatments, the treatment to be performed with the blood purification apparatus B can be recognized by identifying which of the openings (H1 to H4) are used for securing.

The holding portions 3 are attached to each of the edge portions (inclined surfaces 2a) on the two opposite sides of the body 2. The flexible tubes (r) that allow liquids to flow through are placed in the central portion 2b positioned between the holding portions 3 on one of the edge portions (inclined surfaces 2a) and the holding portions 3 on the other of the edge portions (inclined surfaces 2a). Therefore, the arrangement of the flexible tubes (r) can be prevented from becoming complicated, and the limited space can be used efficiently.

The central portion 2b according to the present embodiment has the recess T that is open on the rear side in such a manner as to receive the flexible tubes (r), with the front side thereof covering the flexible tubes (r). Therefore, the flexible tubes (r) can be placed in the recess T. Furthermore, since the flexible tubes (r) are covered by the central portion 2b on the front side, interference between the flexible tubes (r) and other devices or the like can be prevented. It is preferable that the body 2 be transparent in at least the central portion thereof. In such a case, in addition to the prevention of interference between the flexible tubes (r) covered by the central portion 2b and other devices or the like, visual checking of the presence/absence of liquids in the flexible tubes (r) can be facilitated through the transparent central portion 2b.

As illustrated in FIGS. 18 and 19, the central portion 2b may have a recess T that is open on the front side in such a manner as to receive the flexible tubes (r), with the rear side thereof covering the flexible tubes (r). In such a case as well, the flexible tubes (r) can be placed in the recess T. Furthermore, the flexible tubes (r) placed in the central portion 2b can be visually checked directly. Note that the central portion 2b according to the present embodiment has the securing parts (the openings (H1 to H4)) where the flexible tubes (r) are to be secured. Therefore, the flexible tubes (r) can be placed assuredly within the area defined as the central portion 2b. Consequently, accidental displacement of the flexible tubes (r) placed in the central portion 2b to another area can be prevented.

The securing parts (the securing parts provided in the central portion 2b) according to the present embodiment are the openings (H1 to H4) through which the flexible tubes (r) are allowed to pass, and the flexible tubes are securable by being passed through the openings (H1 to H4). Therefore, the flexible tubes (r) can be placed assuredly within the area defined as the central portion 2b. Moreover, no space is necessary for securing the flexible tubes (r). Consequently, the increase in the size of the body can be avoided.

While some embodiments have been described above, the present teachings are not limited thereto. For example, as illustrated in FIG. 22, the body 2 may have a slit t that connects each pair of openings. In such a case, the work of passing the flexible tubes (r) through the respective pairs of openings (H1 to H4) can be facilitated. Furthermore, which of the openings (H1 to H4) are paired can be recognized clearly. Therefore, the occurrence of a situation where the flexible tubes (r) may be passed through wrong openings (H1 to H4) can be suppressed.

While the above embodiments each concern a case where the openings (H1 to H4) as the securing parts for securing the flexible tubes (r) are provided in the central portion 2b of the body 2, the securing parts may be in another form or may be omitted. The holding portions 3 according to each of the above embodiments are continuous with and folded with respect to the body 2 and are rockable about the folds K. Alternatively, the holding portions 3 may be formed on the body 2 continuously therewith in such a manner as not to be rockable (displaceable). The positions of the positioning pin (g) and the positioning hole (h) may be defined arbitrarily. Moreover, the present teachings may be applied to a blood purification apparatus B including no positioning pin (g), with the attaching member 1 having no positioning hole (h).

The attaching member may have other additional functions or the like, as long as holding portions are attached to edge portions on two opposite sides of a body, and flexible tubes that each allow liquid to flow through are to be placed in a central portion of the body, the central portion being positioned between the holding portion on one of the edge portions and the holding portion on the other of the edge portions.

REFERENCE SIGN LIST 1 attaching member
2 body
2a inclined surface
2b central portion
3 holding portion
3a holding groove
3b anchoring hole (anchoring part)
K fold (rocking axis)
A anchor member
Aa anchor hook
Ab pushing portion
B blood purification apparatus (monitoring apparatus)
Ba predetermined position
C pump tube
D connector
M monitor
P peristaltic pump
S stator
Sa fitting recess
R rotor
Ra roller
a1, b1 upper guide pin
a2, b2 lower guide pin
L rotating shaft
g positioning pin
h positioning hole
H1 to H4 opening
H lid

The invention claimed is:

1. An attaching member to be attached to a blood purification apparatus including peristaltic pumps, the attaching member holding pump tubes to be squeezed in a predetermined direction by the respective peristaltic pumps for liquid delivery, the attaching member comprising:
a body attachable to a predetermined position of the blood purification apparatus, the body comprising a central portion and edge portions; inclined surfaces attached to opposing sides of the central portion and extending from the central portion toward the edge portions on opposing sides of the body; and
holding portions carried on the inclined surfaces, the holding portions hold the pump tubes,
wherein flexible tubes that each allow liquid to flow through are to be placed in the central portion of the body, the central portion being positioned between the holding portion on a first of the edge portions and the holding portion on a second of the edge portions, and the central portion has a recess that is open on a rear side so that the flexible tubes extend into the recess and a front side that covers the flexible tubes.

2. The attaching member according to claim 1, wherein the body is transparent in at least the central portion.

3. The attaching member according to claim 1, wherein the central portion has securing parts where the flexible tubes are to be secured.

4. The attaching member according to claim 3, wherein the securing parts are openings through which the flexible tubes are allowed to pass, and the flexible tubes are securable by being passed through the openings.

5. A blood purification circuit connected to one of the pump tubes according to claim 1, the blood purification circuit comprising a blood circuit through which blood is caused to extracorporeally circulate, and a flow route through which substitution fluid is introduced into the blood circuit or a flow route through which dialysate is introduced into a blood purifier connected to the blood circuit or drain liquid is discharged from the blood purifier.

6. The attaching member according to claim 1, wherein the body and the holding portions are one piece that are formed together, wherein folds are located along a boundary between where the body and the holding portions connect and the holding portions are foldable relative to the body so that the holding portions are foldable to a front face of the body.

7. The attaching member according to claim 1, wherein the holding portions have holding grooves and each of the holding grooves comprise connectors that connect to ends of the pump tubes located within the holding portions.

* * * * *